US009907789B2

(12) United States Patent
Tanoue et al.

(10) Patent No.: US 9,907,789 B2
(45) Date of Patent: Mar. 6, 2018

(54) SUSTAINED-RELEASE PREPARATION

(71) Applicant: Takeda Pharmaceutical Company Limited, Chuo-ku, Osaka-shi, Osaka (JP)

(72) Inventors: Yutaka Tanoue, Osaka (JP); Yusuke Murakawa, Osaka (JP); Yumiko Ishii, Osaka (JP); Kaoru Takenaka, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/352,785

(22) PCT Filed: Oct. 19, 2012

(86) PCT No.: PCT/JP2012/077662
§ 371 (c)(1),
(2) Date: Apr. 18, 2014

(87) PCT Pub. No.: WO2013/058409
PCT Pub. Date: Apr. 25, 2013

(65) Prior Publication Data
US 2014/0248362 A1 Sep. 4, 2014

(30) Foreign Application Priority Data

Oct. 21, 2011 (JP) .................................. 2011-232302

(51) Int. Cl.
*A61K 31/4439* (2006.01)
*A61K 9/20* (2006.01)

(52) U.S. Cl.
CPC ........ *A61K 31/4439* (2013.01); *A61K 9/2018* (2013.01); *A61K 9/2031* (2013.01); *A61K 9/2054* (2013.01)

(58) Field of Classification Search
None
See application file for complete search history.

(56) References Cited

U.S. PATENT DOCUMENTS

| 2005/0226928 | A1  |    | 10/2005 | Lodin et al. |       |
|---|---|---|---|---|---|
| 2007/0166376 | A1  |    | 7/2007  | Koike |       |
| 2010/0166853 | A1  | *  | 7/2010  | Bando et al. | 424/456 |
| 2012/0184584 | A1  | *  | 7/2012  | Roses et al. | 514/342 |
| 2016/0133913 | A1  |    | 4/2016  | Murakawa et al. |       |

FOREIGN PATENT DOCUMENTS

| CN | 101269040 A | 9/2008 |
|---|---|---|
| CN | 101884627 A | 11/2010 |
| EP | 0281708 A2 | 9/1988 |
| EP | 0305051 A1 | 3/1989 |
| EP | 0661045 A1 | 7/1995 |
| EP | 1413315 A1 | 4/2004 |
| EP | 1523994 A1 | 4/2005 |
| EP | 1607088 A1 | 12/2005 |
| EP | 1642593 A1 | 4/2006 |
| EP | 2002828 A2 | 12/2008 |
| EP | 2172200 A1 | 4/2010 |
| EP | 2345410 A1 | 7/2011 |
| EP | 2486918 A2 | 8/2012 |
| JP | 64-40424 A | 2/1989 |
| JP | 06-024959 A | 2/1994 |
| JP | 06-024991 A | 2/1994 |
| JP | 06-316517 A | 11/1994 |
| JP | 07-215869 A | 8/1995 |
| JP | 2004-292427 A | 10/2004 |
| JP | 2004-300149 A | 10/2004 |
| JP | 2005-015477 A | 1/2005 |
| JP | 2006-502187 A | 1/2006 |
| JP | 2008-511609 A | 4/2008 |
| JP | 2008-540451 A | 11/2008 |
| JP | 2009-534292 A | 9/2009 |
| JP | 2010-518028 A | 5/2010 |
| JP | 2013-507356 A | 3/2013 |
| WO | WO 94/06414 A1 | 3/1994 |
| WO | WO 98/56359 A2 | 12/1998 |
| WO | WO 00/32190 A1 | 6/2000 |
| WO | WO 2004/026241 A2 | 4/2004 |
| WO | WO 2004/035020 A2 | 4/2004 |
| WO | WO 2004/045608 A1 | 6/2004 |
| WO | WO 2004/078212 A1 | 9/2004 |
| WO | WO 2005/099760 A1 | 10/2005 |
| WO | WO 2006/024949 A2 | 3/2006 |
| WO | WO 2006/119498 A2 | 11/2006 |
| WO | WO 2007/038112 A2 | 4/2007 |
| WO | WO 2007/054976 A2 | 5/2007 |
| WO | WO 2007/072992 A2 | 6/2007 |
| WO | WO 2007/114376 A1 | 10/2007 |
| WO | WO 2007/126135 A1 | 11/2007 |
| WO | WO 2008/095263 A1 | 8/2008 |
| WO | WO 2010/039690 A1 | 4/2010 |
| WO | WO 2012/096873 A1 | 7/2012 |
| WO | WO 2013/058409 A1 | 4/2013 |

OTHER PUBLICATIONS http://www.dictionary.com/browse/sustained-release referenced on Mar. 10, 2016.*
Mantada et al., "Formulation and in vitro evaluation of sustained release matrix tablets of pioglitazone hydrochloride," IJDFR, Jul.-Aug. 2011, 2(4):296-311.
Patidar et al., "Formulation and Evaluation of Pioglitazone Hydrochloride Matrix Tablet Containing Aloe Barbadensis Miller Mucilage Natural Antidiabetic Agent," IJDDHR, Jul.-Sep. 2011, 1(3):157-163.
Sato et al., "Efficacy of PPAR-γ agonist pioglitazone in mild Alzheimer disease," Neurobiology of Aging, 2011, 32:1626-1633.

(Continued)

*Primary Examiner* — Jessica Worsham
(74) *Attorney, Agent, or Firm* — Foley & Lardner LLP

(57) ABSTRACT

Provided is a sustained-release preparation containing pioglitazone or a salt thereof as an active ingredient and showing superior sustainability. A sustained-release preparation containing pioglitazone or a salt thereof, which shows a dissolution ratio of pioglitazone of average 25-58% at the 2-hour time point, and average 60-100% at the 4-hour time point, in a dissolution test according to the 50 rpm USP Paddle Method and using pH 2.0 KCl/HCl buffer at 37° C. as a test solution.

10 Claims, 8 Drawing Sheets

(56) References Cited

OTHER PUBLICATIONS

Chirag et al., "Formulation and Evaluation of Sustained Release Bilayer Tablets of Metformin HCL and Pioglitazone HCL," World Journal of Pharmaceutical Research, 2012, 1(2):242-257.

Chowdary et al., "Design and Evaluation of Floating Tablets of Pioglitazone Employing Selected Natural and Synthetic Polymers," Journal of Pharmacy Research, 2012, 5(2):1240-1242.

Devi et al., "Reclinical Pharmacokinetic Evaluation of Pioglitazone Floating Tablets Formulated Employing Cross-Linked Starch-Urea," International Journal of Pharmacy and Pharmaceutical Sciences, 2012, 4(Suppl. 1):104-106.

Gajula et al., "Formulation and Evaluation of Sustained Release Floating Tablets of Pioglitazone Employing Olibanum Gum and HPMC," Asian Journal of Pharmaceutical and Clinical Research, 2012, 5(1):157-160.

Goswami et al., "Formulation and evaluation of combined floating bilayer tablet of metformin and pioglitazone," Journal of Pharmacy Research, 2011, 4(3):645-646.

Ohmori et al. "Formulation design and the manufacturing method of sustained-release bilayer caplets containing the hydroxypropylmethylcellulose (HPMC) 2208 matrix," Pharm Tech Japan, 2001, 17(7):93-105, with English summary on first page and full English translation.

Patan et al,. "Formulation and Release Characteristic of a Bilayer Matrix Tablet Containing Pioglitazone Hydrochloride as Immediate Release Layer and Metformin Hydrochloride as Sustained Release Layer," Journal of Pharmacy Resarch, 2011, 4(12):4562-4565.

Rao et al., "Design and Evaluation of Pioglitazone Hydrochloride Gastroretentive Floating Matrix Tablet," Asian Journal of Pharmaceutical and Clinical Research, 2012, 5(4):225-231.

Shahi et al., "Formulation and Evaluation of Bilayered Tablet of Metformin Hydrochloride and Pioglitazone Hydrochloride," International Journal of Pharmacy and Pharmaceutical Sciences, 2012, 4(5):380-385.

\* cited by examiner

Plasma concentration profiles of pioglitazone after administration of pioglitazone 1mg sustained release tablets under fasting conditions Plasma concentration profiles of pioglitazone after administration of pioglitazone 1mg sustained release tablets under fed conditions Dissolution profiles of various doses of pioglitazone sustained release tablets

SUSTAINED-RELEASE PREPARATION

TECHNICAL FIELD OF THE INVENTION

The present invention relates to a sustained-release preparation containing pioglitazone or a salt thereof.

BACKGROUND OF THE INVENTION

Patent document 1 discloses a pharmaceutical composition comprising a therapeutically effective amount of a drug, a solubilizer and a release modulator, wherein the release of the drug and the solubilizer is synchronized. However, the document does not describe a matrix tablet-type sustained-release preparation relating to pioglitazone.

Patent document 2 discloses a preparation comprising a core component comprising at least one water-soluble active ingredient, a lipid system comprising at least one lipid, at least one water-insoluble release modifier, at least one channel forming factor, in some cases, one or more pharmaceutical additives and one or more coating factors. However, the document does not describe a matrix tablet-type sustained-release preparation relating to pioglitazone.

Patent document 3 discloses a hydrogel-type sustained-release preparation comprising (1) at least one drug, (2) an additive for penetration of water into the core of the preparation and (3) a hydrogel-forming polymer, wherein said preparation is capable of undergoing substantially complete gelation during its stay in the upper digestive tract including stomach and small intestine and is capable of releasing the drug in the lower digestive tract including colon. However, the document does not describe a matrix tablet-type sustained-release preparation relating to pioglitazone.

The preparation of patent document 3 achieves a stable sustained-release effect, since the drug is dissolved and absorbed fine also in the colon. Since pioglitazone shows low absorbability in the colon, it is not suitable for direct application.

DOCUMENT LIST

Patent Documents

Patent document 1: JP-A-2008-540451
Patent document 2: WO2007/054976
Patent document 3: WO94/06414

SUMMARY OF THE INVENTION

Problems to be Solved by the Invention

Pioglitazone hydrochloride has been widely used in clinical practice over the years as an antidiabetes drug extremely superior in both the treatment effect and safety, and acquired high evaluation. Specifically, it is provided in clinical practice as an immediate-release preparation.

Application of pioglitazone hydrochloride to delay the onset of Alzheimer's disease has been considered. The present inventors have studied a sustained-release preparation, taking into consideration the long-term administration of pioglitazone hydrochloride to patients, including prophylactic use for Alzheimer's disease.

Sustained-release preparations are hoped to provide the following effects.

(1) A sustained release of a medicament can be done; even if the dose is low, stable efficacy can be produced, since the medicament is released in a sustained manner.
(2) The maximum drug concentration (hereinafter sometimes to be indicated as Cmax) can be controlled (e.g., can be suppressed lower than immediate-release preparation).
(3) When combined with the area under plasma concentration-time curve (hereinafter sometimes to be indicated as AUC) equivalent to that of immediate-release preparation, sufficient efficacy can be produced.
(4) A preparation capable of standing physical stimulation due to eating (unsusceptible to stimulation by eating) is expected to be provided.

The present invention aims to provide a sustained-release preparation containing pioglitazone or a salt thereof, which provides the above-mentioned effects (1)-(4).

Means of Solving the Problems

The present inventors have conducted intensive studies in an attempt to solve the above-mentioned problems, and found that a preparation containing pioglitazone or a salt thereof, a gel forming polymer, and a gel forming promoter can solve the above-mentioned problem, which resulted in the completion of the present invention. Furthermore, they have also found that a preparation containing pioglitazone or a salt thereof, and having the below-mentioned particular dissolution property, is particularly preferable from the aspects of the prophylaxis and/or treatment of Alzheimer's disease.

Accordingly, the present invention is as follows.

[1] A sustained-release preparation comprising pioglitazone or a salt thereof, which shows a dissolution ratio of pioglitazone of average 25-58% at the 2-hour time point, and average 60-100% at the 4-hour time point, preferably average 25-58% at the 2-hour time point, average 60-100% at the 4-hour time point, and average 80-110% at the 6-hour time point, in a dissolution test according to the 50 rpm USP Paddle Method and using pH 2.0 KCl/HCl buffer at 37° C. as a test solution.

[2] The sustained-release preparation of the above-mentioned [1], comprising 0.1-8 mg of pioglitazone; or a salt of pioglitazone corresponding to 0.1-8 mg as pioglitazone.

[3] The sustained-release preparation of the above-mentioned [1], comprising 0.1 mg, 0.3 mg, 0.5 mg, 0.8 mg, 2.8 mg or 5.2 mg of pioglitazone; or a salt of pioglitazone corresponding to 0.1 mg, 0.3 mg, 0.5 mg, 0.8 mg, 2.8 mg or 5.2 mg as pioglitazone.

[4] The sustained-release preparation of any of the above-mentioned [1]-[3], wherein the pioglitazone or a salt thereof is pioglitazone hydrochloride.

[5] The sustained-release preparation of any of the above-mentioned [1]-[4], further comprising a gel forming polymer and a gel forming promoter.

[6] The sustained-release preparation of the above-mentioned [5], wherein the gel forming polymer is polyethylene oxide.

[7] The sustained-release preparation of the above-mentioned [6], wherein the polyethylene oxide is 1) contained such that the product of the weight average molecular weight $\times 1/10000$ and the content (%) of polyethylene oxide in the preparation is from $(7 \times M + 1500)$ to $(14.5 \times M + 5410)$, wherein M shows a value calculated by a weight average molecular weight of polyethylene oxide $\times 1/10000$ when one kind of polyethylene oxide is used; or 2) contained such that the product of the weight average molecular weight $\times 1/10000$ and the content (%) of polyethylene oxide having the highest average molecular weight in the preparation is from $(14 \times M - 300)$ to $(17 \times M + 7700)$, wherein M shows a value calculated by a weight average molecular weight of polyethylene oxide having the highest average molecular weight among the polyethylene oxides used ×1/10000 when two or more kinds of polyethylene oxides having different average molecular weights are used.

[8] The sustained-release preparation of any of the abovementioned [5]-[7], wherein the gel forming promoter is a water-soluble hydrophilic base or water-insoluble hydrophilic base.

[9] The sustained-release preparation of the abovementioned [8], wherein the water-soluble hydrophilic base is one kind or a combination of two or more kinds selected from lactose, glucose, mannitol and trehalose, and the water-insoluble hydrophilic base is one kind or a combination of two or more kinds selected from starch, partially pregelatinized starch, crospovidone, crystalline cellulose, carmellose calcium and carmellose.

[10] The sustained-release preparation of any of the abovementioned [1]-[9], which is a tablet.

[11] The sustained-release preparation of the abovementioned [10], which has a tablet weight of 60-600 mg.

[12] The sustained-release preparation of any of the abovementioned [1]-[11], wherein the pioglitazone or a salt thereof has an average particle size of 1 to 25 μm.

[13] A sustained-release preparation comprising pioglitazone or a salt thereof, a gel forming polymer and a gel forming promoter.

[14] The sustained-release preparation of the abovementioned [13], wherein the gel forming polymer is polyethylene oxide.

[15] The sustained-release preparation of the abovementioned [14], wherein the polyethylene oxide is
1) contained such that the product of the weight average molecular weight ×1/10000 and the content (%) of polyethylene oxide in the preparation is from (7×M+1500) to (14.5×M+5410), wherein M shows a value calculated by a weight average molecular weight of polyethylene oxide ×1/10000 when one kind of polyethylene oxide is used; or
2) contained such that the product of the weight average molecular weight ×1/10000 and the content (%) of polyethylene oxide having the highest average molecular weight in the preparation is from (14×M−300) to (17×M+7700), wherein M shows a value calculated by a weight average molecular weight of polyethylene oxide having the highest average molecular weight among the polyethylene oxides used ×1/10000 when two or more kinds of polyethylene oxides having different average molecular weights are used.

[16] The sustained-release preparation of the abovementioned [14], wherein the polyethylene oxide has a weight average molecular weight of not less than 1,000,000 and less than 4,000,000, and is contained at a ratio of 10-90 wt % of the preparation.

[17] The sustained-release preparation of the abovementioned [14], wherein the polyethylene oxide has a weight average molecular weight of not less than 1,000,000 and less than 4,000,000, and is contained at a ratio of 50-80 wt % of the preparation.

[18] The sustained-release preparation of the abovementioned [14], wherein the polyethylene oxide has a weight average molecular weight of not less than 4,000,000 and not more than 10,000,000, and is contained at a ratio of 5-70 wt % of the preparation.

[19] The sustained-release preparation of any of the abovementioned [13]-[18], wherein the gel forming promoter is a water-soluble hydrophilic base or water-insoluble hydrophilic base.

[20] The sustained-release preparation of the abovementioned [19], wherein the water-soluble hydrophilic base is one kind or a combination of two or more kinds selected from lactose, glucose, mannitol and trehalose, and the water-insoluble hydrophilic base is one kind or a combination of two or more kinds selected from starch, partially pregelatinized starch, crospovidone, crystalline cellulose, carmellose calcium and carmellose.

[21] The sustained-release preparation of any of the abovementioned [13]-[20], which is a tablet.

[22] The sustained-release preparation of the abovementioned [21], which has a tablet weight of 60-600 mg.

[23] The sustained-release preparation of any of the abovementioned [13]-[22], comprising 0.1-8 mg of pioglitazone; or a salt of pioglitazone corresponding to 0.1-8 mg as pioglitazone.

[24] The sustained-release preparation of the abovementioned [23], comprising 0.1 mg, 0.3 mg, 0.5 mg, 0.8 mg, 2.8 mg or 5.2 mg of pioglitazone; or a salt of pioglitazone corresponding to 0.1 mg, 0.3 mg, 0.5 mg, 0.8 mg, 2.8 mg or 5.2 mg as pioglitazone.

[25] The sustained-release preparation of any of the abovementioned [1]-[24], wherein the pioglitazone or a salt thereof is pioglitazone hydrochloride.

[26] The sustained-release preparation of any of the abovementioned [13]-[25], wherein the pioglitazone or a salt thereof has an average particle size of 1-25 μm.

[27] A method of producing a sustained-release preparation, comprising
a step of granulating a mixture containing pioglitazone or a salt thereof, a gel forming promoter and a gel forming polymer while spraying an aqueous solution or dispersion containing a gel forming promoter, and compression-molding the obtained mixture;
a step of granulating a mixture containing a gel forming promoter and a gel forming polymer while spraying an aqueous solution or dispersion containing a gel forming promoter, mixing the obtained granules with pioglitazone or a salt thereof, and compression-molding the obtained mixture; or
a step of compression-molding a mixture containing pioglitazone or a salt thereof, a gel forming promoter and a gel forming polymer.

[28] A method of producing a sustained-release preparation, comprising
a step of granulating a mixture containing pioglitazone or a salt thereof, a gel forming promoter and polyethylene oxide while spraying an aqueous solution or dispersion containing a gel forming promoter, and compression-molding the obtained granules;
a step of granulating a mixture containing a gel forming promoter and polyethylene oxide while spraying an aqueous solution or dispersion containing a gel forming promoter, mixing the obtained granules with pioglitazone or a salt thereof, and compression-molding the obtained mixture; or
a step of compression-molding a mixture containing pioglitazone or a salt thereof, a gel forming promoter and polyethylene oxide.

[29] The sustained-release preparation of any of the abovementioned [1]-[26], which is used for the prophylaxis and/or treatment (including delaying onset and suppression of progression) of Alzheimer's disease.

[30] A method of the prophylaxis and/or treatment (including delaying onset and suppression of progression) of Alzheimer's disease, comprising administering the sustained-release preparation of any of the above-mentioned [1]-[26] to a subject in need of the administration thereof.

Effect of the Invention

The sustained-release preparation containing pioglitazone or a salt thereof of the present invention affords the following effects. (1) A sustained release of a medicament can be done; even if the dose is low, stable efficacy can be expected, since the medicament is released in a sustained manner. (2) The maximum drug concentration (Cmax) can be controlled (e.g., can be suppressed lower than immediate-release preparation). (3) The area under plasma concentration-time curve (AUC) equivalent to that of immediate-release preparation can be achieved. (4) A preparation capable of standing physical stimulation due to eating (unsusceptible to stimulation by eating) is hoped to be provided.

DESCRIPTION OF EMBODIMENTS

Figure 1:
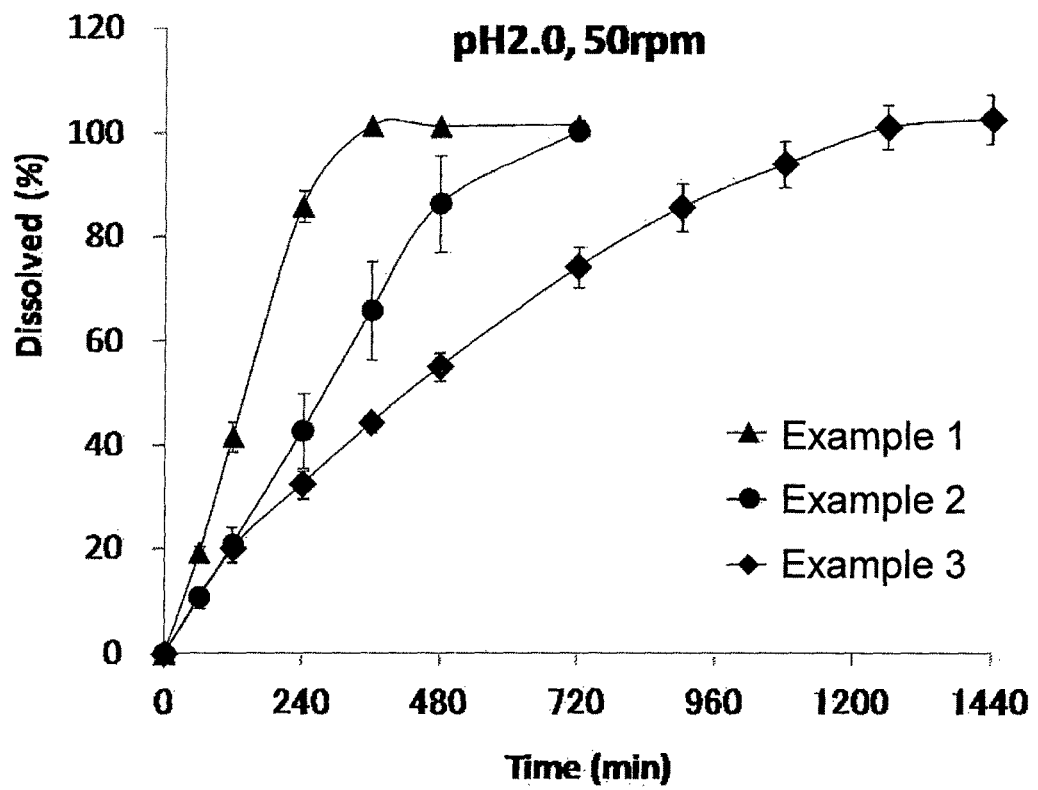
FIG. 1 shows the results in Experimental Example 1.

The present invention is explained in detail in the following.

In the "pioglitazone or a salt thereof" to be used in the sustained-release preparation of the present invention, examples of the salt of pioglitazone include pharmacologically acceptable salts such as salts with inorganic acids, salts with organic acids, salts with acidic amino acids and the like.

Preferable examples of the salts with inorganic acids include salts with hydrochloric acid, hydrobromic acid, nitric acid, sulfuric acid, phosphoric acid and the like.

Preferable examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salts with acidic amino acids include salts with aspartic acid, glutamic acid and the like.

In addition, the pioglitazone may be an anhydride or a hydrate, which may be further labeled with an isotope (e.g., $^3H$, $^{14}C$, $^{35}S$, $^{125}I$) and the like.

The pioglitazone or a salt thereof is particularly preferably pioglitazone hydrochloride.

The pioglitazone or a salt thereof may be diluted with a diluent generally used in the medical care, food field and the like, and the like.

Generally, since a powder is an assembly of particles having various sizes, the size of a particle is shown by an average particle size. As the average particle size, median size, mode diameter, arithmetic mean diameter and the like are used. The median size is also indicated as d50, and means a particle size that divides coarse granules and fine granules into 50% each in weight distribution or number distribution. The average particle size used in the present specification is mostly shown in the median size.

The measurement method of a powder includes laser diffraction method, dynamic light scattering method, centrifugal sedimentation method, FFF method, electrical sensing zone method and the like. The laser diffraction method-particle size distribution measuring apparatus includes Mastersizer 2000 (manufactured by Malvern Instruments Ltd.), HELOS&RODOS (manufactured by SYMPATEC), SALD2200 (manufactured by Shimadzu Corporation), LA-920 (manufactured by Horiba, Ltd.) and the like. The average particle size in the present specification is a value measured by Mastersizer 2000 based on the laser diffraction method.

In the sustained-release preparation of the present invention, the average particle size of pioglitazone or a salt thereof to be used as a drug substance is generally 1-25 μm, preferably 2-21 μm, more preferably 2-10 μm. Using such average particle size, a preparation superior in absorbability can be obtained.

The above-mentioned preferable average particle size is applied to pioglitazone or a salt thereof to be used as a drug substance (including pulverized products obtained by pulverization in the process of producing a sustained-release preparation and the like) for producing the sustained-release preparation of the present invention. That is, the average particle size of pioglitazone or a salt thereof may vary beyond the above-mentioned range due to coagulation and the like of pioglitazone or a salt thereof in the process of producing the sustained-release preparation of the present invention or a process of preserving the sustained-release preparation after production. The pulverization is performed by using a preparation equipment such as mortar, jet mill, hammer mill, screen mill and the like.

While the content of pioglitazone or a salt thereof in the sustained-release preparation of the present invention varies depending on the dosage form of the sustained-release preparation, target disease, severity of disease, and the like, it is an amount generally corresponding to 0.1-45 mg, preferably 0.1-30 mg, more preferably 0.1-15 mg, still more preferably 0.1-10 mg, further more preferably 0.1-8 mg, as pioglitazone. Such content is suitable for the prophylaxis and/or treatment of, for example, Alzheimer's disease. The preparation only needs to be administered 1-3 times (preferably, once) per day.

More specifically, the sustained-release preparation of the present invention is a preparation comprising 0.1 mg, 0.3 mg, 0.5 mg, 0.8 mg, 2.8 mg or 5.2 mg of pioglitazone; or a salt of pioglitazone corresponding to 0.1 mg, 0.3 mg, 0.5 mg, 0.8 mg, 2.8 mg or 5.2 mg as pioglitazone. The preparation is preferably administered once per day.

The content of pioglitazone or a salt thereof in the sustained-release preparation of the present invention is generally 0.05-20 wt %, preferably 0.06-15 wt %, more preferably 0.08-10 wt %, as pioglitazone.

The sustained-release preparation of the present invention can provide a preparation comprising pioglitazone or a salt thereof, which shows a dissolution ratio of pioglitazone of average 25-58% at the 2-hour time point, and average 60-100% at the 4-hour time point, preferably average 25-58% at the 2-hour time point, average 60-100% at the 4-hour time point, and average 80-110% at the 6-hour time point, in a dissolution test according to the 50 rpm USP (US Pharmacopeia) Paddle Method and using pH 2.0 KCl/HCl buffer at 37° C. as a test solution.

With such particular dissolution property, a preparation having the aforementioned effects (1)-(4) and useful for the prophylaxis and/or treatment of Alzheimer's disease can be provided.

The present invention also relates to a sustained-release preparation containing pioglitazone or a salt thereof, a gel forming polymer, and a gel forming promoter.

Examples of the gel forming polymer to be used in the present invention include polyethylene oxide, hypromellose, hydroxypropylcellulose, methylcellulose, carboxymethylcellulose sodium, low-substituted hydroxypropylcellulose, croscarmellose sodium, and the like, with preference given to polyethylene oxide.

Polyethylene oxide to be used in the present invention has a weight average molecular weight of generally 100,000-10,000,000, preferably 300,000-8,000,000.

In the present invention, polyethylene oxide may be a commercially available product. Examples thereof include Polyox WSR-308 (average molecular weight: 8,000,000, viscosity: 10000-15000 cps (1% aqueous solution 25° C.)), Polyox WSR-303 (average molecular weight: 7,000,000, viscosity: 7500-10000 cps (1% aqueous solution 25° C.)), Polyox WSR Coagulant (average molecular weight 5,000,000, viscosity: 5500-7500 cps (1% aqueous solution 25° C.)), Polyox WSR-301 (average molecular weight: 4,000,000, viscosity: 1650-5500 cps (1% aqueous solution 25° C.)), Polyox WSR N-60K (average molecular weight: 2,000,000, viscosity: 2000-4000 cps (2% aqueous solution 25° C.)), Polyox WSR N-12K (average molecular weight: 1,000,000, viscosity: 400-800 cps (2% aqueous solution 25° C.)), Polyox WSR-1105 (average molecular weight: 900,000, viscosity: 8800-17600 cps (5% aqueous solution 25° C.)), Polyox WSR 205 (average molecular weight: 600,000, viscosity: 4500-8800 cps (5% aqueous solution 25° C.)), Polyox WSR N-750 (average molecular weight: 300,000, viscosity: 600-1200 cps (5% aqueous solution 25° C.)), Polyox WSR N-80 (average molecular weight: 200,000, viscosity: 65-115 cps (5% aqueous solution 25° C.)), Polyox WSR N-10 (average molecular weight: 100,000, viscosity: 30-50 cps (5% aqueous solution 25° C.)), UCARFLOC Polymer 310 (average molecular weight: 10,000,000, viscosity: not less than 15000 cps (1% aqueous solution 25° C.)), UCARFLOC Polymer 309 (average molecular weight: 8,000,000, viscosity: 10000-15000 cps (1% aqueous solution 25° C.)), UCARFLOC Polymer 304 (average molecular weight: 7,000,000, viscosity: 7500-10000 cps (1% aqueous solution 25° C.)), UCARFLOC Polymer 302 (average molecular weight: 5,000,000, viscosity: 5500-7500 cps (1% aqueous solution 25° C.)), UCARFLOC Polymer 300 (average molecular weight: 4,000,000, viscosity: 1650-5500 cps (1% aqueous solution 25° C.)) and the like.

In the present invention, when one kind of polyethylene oxide is used and a sustained-release preparation showing a pioglitazone dissolution ratio of "average 25-58% at 2-hour time point, average 60-100% at 4-hour time point, and average 80-110% at 6-hour time point" (hereinafter sometimes to be abbreviated as "Fast formulation") is to be obtained, polyethylene oxide in the sustained-release preparation of the present invention is used in such an amount that sets 1) the upper limit of the product of the weight average molecular weight×$\frac{1}{10000}$ and the content (%) of polyethylene oxide in the preparation to preferably ($14.5 \times M+5410$), more preferably ($14.5 \times M+4970$), still more preferably ($14.5 \times M+4530$), further more preferably ($14.5 \times M+4090$), and 2) the lower limit thereof to preferably ($7 \times M+1500$), more preferably ($7 \times M+1545$), still more preferably ($7 \times M+1590$), and further more preferably ($7 \times M+1600$), wherein M shows a value calculated by "the weight average molecular weight of polyethylene oxide"×"$\frac{1}{10000}$".

For example, when the weight average molecular weight of polyethylene oxide is 1,000,000 (M=100), the upper limit of the product of the weight average molecular weight×$\frac{1}{10000}$ and the content (%) of polyethylene oxide in the preparation is further more preferably $14.5 \times 100 + 4090 = 5540$, and the lower limit thereof is further more preferably $7 \times 100 + 1600 = 2300$. In the sustained-release preparation (Example 1) wherein the weight average molecular weight of polyethylene oxide is 1,000,000 and the content of polyethylene oxide in the preparation is 30%, the product of the weight average molecular weight×$\frac{1}{10000}$ and the content (%) of polyethylene oxide in the preparation is $1000000 \times \frac{1}{10000} \times 30 (\%) = 3000$, and it goes into the range of 2300-5540.

In the present invention, when two or more kinds of polyethylene oxides having different average molecular weights are used in combination, and a sustained-release preparation showing a pioglitazone dissolution ratio of "average 25-58% at 2-hour time point, average 60-100% at 4-hour time point, and average 80-110% at 6-hour time point" is to be obtained, polyethylene oxide having the highest average molecular weight among the polyethylene oxides used in the sustained-release preparation of the present invention is used in such an amount that sets 1) the upper limit of the product of the weight average molecular weight×$\frac{1}{10000}$ and the content (%) of polyethylene oxide having the highest average molecular weight among the polyethylene oxides used in the preparation to preferably ($17 \times M+7700$), more preferably ($17 \times M+6400$), still more preferably ($17 \times M+5100$), and further more preferably ($17 \times M+3500$), and 2) the lower limit thereof to preferably ($14 \times M-300$), more preferably ($14 \times M-100$), still more preferably ($14 \times M+90$), and further more preferably ($14 \times M+270$), wherein M shows a value calculated by "the weight average molecular weight of polyethylene oxide having the highest average molecular weight among the polyethylene oxides used"×"$\frac{1}{10000}$".

The content of polyethylene oxide in the sustained-release preparation of the present invention is generally 10-90 wt %, preferably 20-80 wt %, more preferably 30-80 wt %, of the preparation.

Hypromellose to be used in the present invention has a weight average molecular weight of generally 20,000-500,000, preferably 20,000-250,000.

In the present invention, hypromellose may be a commercially available product and, for example, METHOCEL K100 (average molecular weight: 26,000, 2% viscosity: 100 mPa·sec), METHOCEL K4M (average molecular weight: 86,000, 2% viscosity: 4000 mPa·sec), METHOCEL K15M (average molecular weight: 120,000, 2% viscosity: 15000 mPa·sec), METHOCEL K100M (average molecular weight: 246,000, 2% viscosity: 100000 mPa·sec) and the like can be mentioned.

When a sustained-release preparation showing a pioglitazone dissolution ratio of "average 25-58% at 2-hour time point, average 60-100% at 4-hour time point, and average 80-110% at 6-hour time point" is to be obtained, the content of hypromellose in the sustained-release preparation of the present invention is 10-60 wt % (more preferably 30-50 wt %, still more preferably 30-40 wt %) when the average molecular weight is 26,000; 10-50 wt % (more preferably 20-40 wt %, still more preferably 20-30 wt %) when the average molecular weight is 86,000; 10-50 wt % (more preferably 20-40 wt %, still more preferably 20-30 wt %) when the average molecular weight is 120,000; and 10-50 wt % (more preferably 10-30 wt %, still more preferably 10-20 wt %) when the average molecular weight is 246,000.

When a sustained-release preparation wherein the dissolution ratio of pioglitazone shows the dissolution pattern of the preparation of Example 4 shown in Experimental Example 2 described later (hereinafter sometimes to be abbreviated as Middle formulation) is to be obtained, polyethylene oxide preferably has an average molecular weight of not less than 1,000,000 and less than 4,000,000, and is preferably contained in a proportion of 50-80 wt % in the preparation.

When a sustained-release preparation wherein the dissolution ratio of pioglitazone shows the dissolution pattern of the preparation of Example 5 shown in Experimental Example 2 described later (hereinafter sometimes to be abbreviated as Slow formulation) is to be obtained, polyethylene oxide preferably has an average molecular weight of not less than 4,000,000 and not more than 10,000,000, and is preferably contained in a proportion of 5-70 wt % in the preparation.

In the present specification, the gel forming promoter means an excipient that promotes penetration of water into the preparation before gelling of a gel forming polymer, and is not particularly limited as long as it shows such action. In the sustained-release preparation of the present invention, a part of the gel forming promoter also has a function of a surface modifier.

In the present specification, the surface modifier is not particularly limited as long as it quickens the gelling of a gel forming polymer by surface modification of the gel forming polymer.

Examples of the gel forming promoter to be used in the present invention include water-soluble hydrophilic base and water-insoluble hydrophilic base.

Examples of the water-soluble hydrophilic base to be used in the present invention include sugar and sugar alcohols such as lactose, glucose, mannitol, trehalose, D-sorbitol, xylitol, sucrose, maltose, lactulose, D-fructose, dextran, glucose and the like, water-soluble polymers such as polyethylene glycol (e.g., macrogol 400, macrogol 1500, macrogol 4000, macrogol 6000, macrogol 20000 (all manufactured by NOF Corporation)), polyvinylpyrrolidone (e.g., PVP (registered trade mark) K30 (manufactured by BASF)) and the like, surfactants such as polyoxyethylene hydrogenated castor oil (e.g., Cremophor (registered trade mark) RH40 (manufactured by BASF), HCO-40, HCO-60 (manufactured by Nikko Chemicals)), polyoxyethylenepolyoxypropyleneglycol (for example, Pluronic (registered trade mark) F68 (manufactured by Asahi Denka Kogyo Co., Ltd.) etc.), polyoxyethylene sorbitan higher fatty acid ester (for example, Tween 80 (manufactured by KANTO KAGAKU) etc.) and the like, salts such as sodium chloride, magnesium chloride and the like, organic acids such as citric acid, tartaric acid and the like, amino acids such as glycine, β-alanine, lysine hydrochloride and the like, amino sugars such as meglumine and the like, and the like, and one or more kinds may be used in combination.

Examples of the water-insoluble hydrophilic base to be used in the present invention include starch, cereal flour containing starch (e.g., corn starch, potato starch, wheat starch, rice starch), partially pregelatinized starch, hydroxypropylstarch, crospovidone, crystalline cellulose (CEOLUS KG801, KG802, PH101, PH102, PH301, PH302, PH-F20, RC-A591NF, KG1000, PH101D, PH301D, PH301Z, UF702, UF711 (trade names, manufactured by Asahi Kasei Chemicals Corporation), those called microcrystalline cellulose), fine particle anhydrous silicic acid (light anhydrous silicic acid without hydrophobizing treatment or amorphous silica fine particles with particle size of not more than 0.1 micron), carboxymethylcellulose, carboxymethylcellulose calcium (carmellose calcium), sodium carboxymethyl starch, carmellose sodium, croscarmellose sodium, carmellose, carmellose calcium, low-substituted hydroxypropylcellulose [preferably, low-substituted hydroxypropylcellulose such as LH-11, LH-21, LH-31, LH-22, LH-32, LH-20, LH-30, LH-33, LH-B1, NBD-020, NBD-021, NBD-022 (trade names, manufactured by Shin-Etsu Chemical Co., Ltd.) and the like, which have a hydroxypropoxy group content of 5-16 wt %] and the like, and one or more kinds may be used in combination.

The content of the gel forming promoter in the sustained-release preparation of the present invention is generally 2.5-80 wt %, preferably 5-80 wt %, more preferably 15-80 wt %.

In the sustained-release preparation of the present invention, Cmax after oral administration of the sustained-release preparation containing 1 mg of pioglitazone to a beagle under fasting conditions (pentagastrin treatment) is preferably within the range of generally 5-90%, more preferably 10-80%, still more preferably 20-70%, as compared to immediate-release tablets. Under the same conditions, AUC is preferably within the range of 30-150%, more preferably 40-120%, still more preferably 50-110%, as compared to immediate-release tablets.

In the sustained-release preparation of the present invention, moreover, Cmax after oral administration of the sustained-release preparation containing 1 mg of pioglitazone to a beagle under food ingestion conditions (after fasting for not less than 18 hr from the previous day of administration, a solid feed (about 50 g) impregnated with water (about 80 ml) is given, at about 1 hr after feeding, tablet is administered by gavage, and water (60 ml) is given) is preferably within the range of generally 10-120%, more preferably 30-120%, still more preferably 50-120%, as compared to immediate-release tablets. Under the same conditions, AUC is preferably within the range of 50-150%, more preferably 60-140%, still more preferably 70-130%, as compared to immediate-release tablets.

The above-mentioned numerical values are calculated based on the evaluation results of the preparation of the below-mentioned Comparative Example 1 as an immediate-release tablet and the sustained-release preparation of the present invention according to the test method described in Experimental Examples 3 and 4.

The average value of the maximum drug concentration (Cmax) when the sustained-release preparation of the present invention (containing 1 mg of pioglitazone) is orally administered to a beagle under fasting, which was treated with pentagastrin, is 10-130 (ng/mL), and the average value of The area under plasma concentration-time curve (AUC) is preferably 70-470 (ng min/mL).

The sustained-release preparation of the present invention optionally contains an additive conventionally used in the technical field of preparations. Examples of the additive include excipient, disintegrant, binder, lubricant, colorant, pH adjuster, surfactant, stabilizer, corrigent, sweetener, flavor, fluidizer, antistatic agent, light shielding agent, antioxidant, reducing agent, chelating agent and the like. These additives are used in an amount conventionally used in the technical field of preparations. In addition, two or more kinds of these additives may be mixed at an appropriate ratio and used.

Examples of the excipient include crystalline cellulose, anhydrous calcium phosphate, anhydrous dibasic calcium phosphate, calcium hydrogen phosphate, precipitated calcium carbonate, calcium silicate, powder cellulose, gelatin, light anhydrous silicic acid (e.g., light anhydrous silicic acid without hydrophobizing treatment or amorphous silica fine particle with a particle size greater than 0.1 micron), synthetic aluminum silicate, magnesium alumino metasilicate, magnesium oxide, calcium phosphate, calcium carbonate and calcium sulfate. Of these, crystalline cellulose is preferable.

Examples of the crystalline cellulose include CEOLUS KG801, KG802, PH101, PH102, PH301, PH302, PH-F20, RC-A591NF (trade names, manufactured by Asahi Kasei Chemicals Corporation), including those called microcrystalline cellulose.

Examples of the disintegrant include carboxymethylcellulose, carboxymethylcellulose calcium (carmellose calcium), sodium carboxymethyl starch, carmellose sodium, croscarmellose sodium, low-substituted hydroxypropylcellulose [preferably, low-substituted hydroxypropylcellulose having a hydroxypropoxy group content of 5-16 wt % such as LH-11, LH-21, LH-31, LH-22, LH-32, LH-20, LH-30, LH-33, LH-B1, NBD-020, NBD-021, NBD-022 (trade names, manufactured by Shin-Etsu Chemical Co., Ltd.) and the like].

Examples of the binder include hydroxypropylcellulose [preferably, HPC-SSL, SL, L (trade names, NIPPON SODA CO., LTD.)], hydroxypropylmethylcellulose, povidone (polyvinylpyrrolidone), gum arabic powder, gelatin, pullulan, methylcellulose, crystalline cellulose, low-substituted hydroxypropylcellulose [preferably, low-substituted hydroxypropylcellulose having a hydroxypropoxy group content of 5-16 wt % such as LH-11, LH-21, LH-31, LH-22, LH-32, LH-20, LH-30, LH-33, LH-B1, NBD-020, NBD-021, NBD-022 (trade names, manufactured by Shin-Etsu Chemical Co., Ltd.) and the like], dextran, and polyvinyl alcohol.

Examples of the lubricant include stearic acid, magnesium stearate, calcium stearate, talc, sucrose esters of fatty acids, sodium stearyl fumarate, waxes, DL-leucine, sodium lauryl sulfate, magnesium lauryl sulfate, macrogol and light anhydrous silicic acid (light anhydrous silicic acid without hydrophobizing treatment or amorphous silica fine particle with a particle size greater than 0.1 micron). Of these, sodium stearyl fumarate is preferable.

Examples of the colorant include food colors such as Food Color Yellow No. 5 (Sunset Yellow, same as US Food Color yellow No. 6), Food Color Red No. 2, Food Color Blue No. 2 and the like, food lake colors, yellow ferric oxide (yellow ferric oxide pigment), red ferric oxide (red ferric oxide pigment), black ferric oxide (black ferric oxide pigment), riboflavin, riboflavin organic acid ester (e.g., riboflavin butyric acid ester), riboflavin phosphate or alkali metal or alkaline earth metal salt thereof, phenolphthalein, titanium oxide, lycopene and beta-carotene.

Examples of the pH adjuster include citrate, phosphate, carbonate, tartrate, fumarate, acetate and amino acid salt.

Examples of the surfactant include sodium lauryl sulfate, polysorbate 80, polyoxyethylene(160)polyoxypropylene(30)glycol, polyoxyethylene(196)polyoxypropylene(67)glycol and polyoxyethylene hydrogenated castor oil 60.

Examples of the stabilizer include sodium ascorbate, tocopherol, tetrasodium edetate, nicotinic acid amide, cyclodextrins; alkaline earth metal salt (e.g., calcium carbonate, calcium hydroxide, magnesium carbonate, magnesium hydroxide, magnesium silicate, magnesium aluminate) and butylhydroxyanisole.

Examples of the corrigent include ascorbic acid, (anhydrous) citric acid, tartaric acid and malic acid.

Examples of the sweetener include aspartame, acesulfame potassium, thaumatin, saccharin sodium and dipotassium glycyrrhizinate.

Examples of the flavor include menthol, peppermint oil, lemon oil and vanillin.

Examples of the fluidizer include light anhydrous silicic acid (light anhydrous silicic acid without hydrophobizing treatment or amorphous silica fine particle with a particle size greater than 0.1 micron) and hydrated silicon dioxide. Here, light anhydrous silicic acid only needs to contain hydrated silicon dioxide ($SiO_2 \cdot nH_2O$) (n is an integer) as a main component, and concrete examples thereof include Sylysia 320 (trade name, Fuji Silysia Chemical Ltd.), AEROSIL 200 (trade name, NIPPON AEROSIL) and the like.

Examples of the antistatic agent include talc and light anhydrous silicic acid (light anhydrous silicic acid without hydrophobizing treatment or amorphous silica fine particle with a particle size greater than 0.1 micron).

Examples of the light shielding agent include titanium oxide.

Examples of the antioxidant include butylhydroxytoluene (BHT), butylhydroxyanisole (BHA), tocopherol, tocopherol ester (e.g., tocopherol acetate), ascorbic acid or alkali metal or alkaline earth metal salt thereof, lycopene and beta-carotene.

Examples of the reducing agent include cystine and cysteine.

Examples of the chelating agent include EDTA or alkali metal or alkaline earth metal salt thereof.

The shape of the sustained-release preparation of the present invention is not particularly limited, and may be any such as round, caplet, donut, oblong and the like.

The sustained-release preparation of the present invention can be produced by a method conventionally used in the technical field of preparations and using the above-mentioned various additives.

For example, the sustained-release preparation of the present invention can be produced by mixing pioglitazone or a salt thereof (e.g., pioglitazone hydrochloride), a gel forming promoter (e.g., D-mannitol, lactose), a gel forming polymer (e.g., polyethylene oxide), and an optionally-added excipient, granulating the mixture while spraying an aqueous solution or dispersion of a gel forming promoter (e.g., D-mannitol, lactose), drying the granules, sieving them where necessary, mixing an optionally added lubricant (e.g., sodium stearyl fumarate) therewith, and compression molding the obtained granules or mixture.

In the above-mentioned method, pioglitazone or a salt thereof, and the optionally added excipient may be added after the above-mentioned granulation and drying.

For example, the sustained-release preparation of the present invention can be produced by mixing pioglitazone or a salt thereof (e.g., pioglitazone hydrochloride), a gel forming promoter (e.g., D-mannitol, lactose), a gel forming polymer (e.g., polyethylene oxide), and an optionally-added excipient, mixing an optionally-added lubricant (e.g., sodium stearyl fumarate) therewith, and compression molding the obtained mixture.

Mixing can be performed using a blending machine such as a V-type mixer, a tumbler mixer and the like. Granulation can be performed using, for example, a high speed mixer granulator, a fluid bed dryer granulator and the like. Compression molding can be performed by punching using, for example, a single punch tableting machine, a rotary tableting machine and the like.

The sustained-release preparation of the present invention even in the form of a core tablet can afford sufficiently sustained release. Where necessary, coating may be applied by a method conventionally used in the technical field of preparations. In addition, marks or letters for identification, or further, a separating line for dividing the tablet may be applied.

Examples of the coating base include sugar coating base, water-soluble film coating base, enteric film coating base, sustained-release film coating base and the like.

As the sugar coating base, sucrose is used, and further, one or more kinds selected from talc, precipitated calcium carbonate, gelatin, gum arabic, pullulan, carnauba wax and the like may be used in combination.

Examples of the water-soluble film coating base include cellulose polymers such as hydroxypropylcellulose, hydroxypropylmethylcellulose, hydroxyethylcellulose, methylhydroxyethylcellulose and the like; synthetic polymers such as polyvinyl alcohol, polyvinyl acetal diethyl aminoacetate, aminoalkylmethacrylate copolymer E [Eudragit E (trade name)], polyvinylpyrrolidone and the like; polysaccharides such as pullulan and the like; and the like.

Examples of the enteric film coating base include cellulose polymers such as hydroxypropylmethylcellulose phthalate, hydroxypropylmethylcellulose acetatesuccinate, carboxymethylethylcellulose, cellulose acetate phthalate and the like; acrylic acid polymers such as methacrylic acid copolymer L [Eudragit L (trade name)], methacrylic acid copolymer LD [Eudragit L-30D55 (trade name)], methacrylic acid copolymer S [Eudragit S (trade name)] and the like; naturally occurring substances such as shellac and the like; and the like.

Examples of the sustained-release film coating base include cellulose polymers such as ethylcellulose, acetyl cellulose and the like; acrylic acid polymers such as aminoalkylmethacrylate copolymer RS [Eudragit RS (trade name)], ethyl acrylate-methyl methacrylate copolymer suspension [Eudragit NE (trade name)] and the like; and the like.

Two or more kinds of the above-mentioned coating bases may be mixed at an appropriate ratio and used. In addition, a coating additive may be used for coating.

Examples of the coating additive include light shielding agent and/or colorant such as titanium oxide, talc, red ferric oxide and the like; plasticizers such as polyethylene glycol, triethyl citrate, castor oil, polysorbates and the like; and the like.

The sustained-release preparation of the present invention also has the following effect in addition to the superior effect explained above.

The release rate of the sustained-release preparation of the present invention can be controlled by changing the amount and molecular weight of the gel forming polymer such as polyethylene oxide and the like.

The sustained-release preparation of the present invention can be down-sized and permits zero-order type drug release.

The sustained-release preparation of the present invention can improve stability of pioglitazone or a salt thereof by adding a component with poor compatibility (e.g., citric acid) as a component outside the granule.

The sustained-release preparation of the present invention can achieve rapid gelling since its gel-forming function is improved by encapsulating a component that prevents penetration of water (hydroxy polymer, binder and the like) in granules, and a route of water penetration is secured by covering the component that prevents penetration of water with a surface modifier. As a result, a zero-order drug release becomes possible. Furthermore, the strength necessary for standing the physical stimulation in the body due to eating can be imparted.

When the sustained-release preparation of the present invention contains polyethylene oxide as a gel forming polymer, decomposition of polyethylene oxide due to oxidation can be suppressed by using a gel forming promoter capable of reducing the oxidization tendency of polyethylene oxide.

While the weight of the sustained-release preparation of the present invention is not particularly limited, it is generally 60-600 mg, preferably 60-480 mg, more preferably 60-200 mg, still more preferably 100-200 mg.

The sustained-release preparation of the present invention can be safely administered orally to a mammal (e.g., mouse, rat, rabbit, cat, dog, bovine, horse, monkey, human).

The sustained-release preparation of the present invention can be used for the prophylaxis or treatment (including delay of onset and suppression of progression) of Alzheimer's disease. Alzheimer's disease is one kind of dementia wherein change of personality is the main symptom. As the etiology of Alzheimer's disease, there are theories such as cell degeneration due to intracellular accumulation of β amyloid protein and the like. However, the etiology has not been elucidated, and the symptoms progress in stages along with atrophy of cerebrum, as shown below.

1) Mild Cognitive Impairment (Precursor of Alzheimer)

Mild personality changes such as anxiety, depression, sleep disorder, visual hallucination or delusions and the like appear from about 2-3 years before decline in mental ability. Although light failing memory is observed, no adverse effect is imposed on daily living such as calculation of money, driving a car and the like.

2) Alzheimer First Stage

The first stage is also known as an amnesia stage where amnesia, planotopokinesia, hyperactivity, wandering and the like are observed. As the change of the cells, general function of cerebral cortex starts to fade, and failing memory starts to exceed the level of simple forgetfulness.

3) Alzheimer Second Stage

It is also called a confusion stage, where atrophy of cerebral cortex progresses and the initial symptoms are aggravated further to make conversation difficult and the like. Severe intellectual disability, aphasia, apraxia and agnosia appear. The extrapyramidal symptoms are sometimes mistaken for Parkinson's disease.

4) Alzheimer Third Stage

It is also called a bed rest stage, where the patients are bedridden due to the late stage of severe dementia, and incontinence, apastia, overeating, repetitive motion, spasm and the like as well as aphasia are observed. Since the patients cannot take care of themselves, they require care in life in general.

Since the symptoms of Alzheimer's disease progress gradually, various biomarkers have been proposed to predict and prevent the onset of the disease in early stages. The biomarker includes Aβ 42 (42 residue fragments of β amyloid protein) in cerebrospinal fluid, tau protein in cerebrospinal fluid, number of apolipoprotein E (ApoE) ε4 allele, and the like. It has been reported that TOMM40 (mitochondria outer membrane channel subunit, 40 kDa)

specifically interacts with ApoE colocalized in mitochondria outer membrane and induces mitochondrial apoptosis (PCT/US2009/053373).

The sustained-release preparation of the present invention is desirably administered to patients with a high risk of developing Alzheimer's disease based on such biomarkers, in an effort to prevent the onset of the disease.

The sustained-release preparation of the present invention can be used in combination with an active ingredient other than pioglitazone and a salt thereof (hereinafter sometimes to be abbreviated as concomitant component). In this case, the timing of the administration of pioglitazone or a salt thereof and a concomitant component is not limited, and they may be simultaneously administered to the subject of administration, or administered in a staggered manner. Furthermore, the sustained-release preparation of the present invention and a concomitant component may be administered as two kinds of preparations containing each active ingredient, or as a single preparation containing both active ingredients.

The dose of the concomitant component can be appropriately determined by reference to the clinically employed doses.

Using a concomitant component, superior effects can be obtained such as 1) effect of enhancing the action of the sustained-release preparation of the present invention or a concomitant component (synergistic effect of medicament action), 2) effect of decreasing the dose of the sustained-release preparation of the present invention or a concomitant component (as compared to single administration), 3) effect of decreasing the secondary action of the sustained-release preparation of the present invention or a concomitant component and the like.

As the concomitant component, other medicaments useful as an agent for the prophylaxis and/or treatment of Alzheimer's disease can be mentioned.

EXAMPLES

The present invention is explained in more detail in the following by referring to Examples, Comparative Examples, Reference Examples and Experimental Examples, which are not to be construed as limitative.

Example 1

In a fluid bed dryer granulator (MP-01, POWREX), and according to the formulation of Table 1, pioglitazone hydrochloride (fine pulverized product, average particle size about 5 μm), microcrystalline cellulose, D-mannitol (in Table 1, D-mannitol-1) and polyethylene oxide (Polyox WSR N12-K, Dow chemical company) were uniformly mixed, and the mixture was granulated while spraying an aqueous solution of D-mannitol (in Table 1, D-mannitol-2) and dried in the granulator. The obtained granules were sieved using a 16M sieve to give a sieved powder. To the sieved powder was added sodium stearyl fumarate, and the mixture was admixed by hand in a 10 L plastic bag to give granules for tableting. The granules were tableted in weight 120 mg by a rotary tableting machine (Correct 19K, Kikusui Seisakusho Ltd.) with a 7 mmϕ punch to give 3,000 core tablets containing 1 mg of pioglitazone per tablet.

TABLE 1

| additive | function | formulation amount (mg/tablet) |
|---|---|---|
| pioglitazone hydrochloride | active ingredient | 1.1 |
| (pioglitazone free form) | | (1) |
| microcrystalline cellulose | gel forming promoter | 0.3 |
| D-mannitol-1 | gel forming promoter | 69.4 |
| D-mannitol-2 | surface modifier | 12 |
| polyethylene oxide | gel forming polymer | 36 |
| sodium stearyl fumarate | lubricant | 1.2 |
| Total | | 120 |

Example 2

In a fluid bed dryer granulator (MP-01, POWREX), and according to the formulation of Table 2, pioglitazone hydrochloride (fine pulverized product, average particle size about 5 μm), microcrystalline cellulose, D-mannitol (in Table 2, D-mannitol-1) and polyethylene oxide (Polyox WSR N12-K, Dow chemical company) were uniformly mixed, and the mixture was granulated while spraying an aqueous solution of D-mannitol (in Table 2, D-mannitol-2) and dried in the granulator. The obtained granules were sieved using a 16M sieve to give a sieved powder. To the sieved powder was added sodium stearyl fumarate, and the mixture was admixed by hand in a 10 L plastic bag to give granules for tableting. The granules were tableted in weight 120 mg by a rotary tableting machine (Correct 19K, Kikusui Seisakusho Ltd.) with a 7 mmϕ punch to give 3,000 core tablets containing 1 mg of pioglitazone per tablet.

TABLE 2

| additive | function | formulation amount (mg/tablet) |
|---|---|---|
| pioglitazone hydrochloride | active ingredient | 1.1 |
| (pioglitazone free form) | | (1) |
| microcrystalline cellulose | gel forming promoter | 0.28 |
| D-mannitol-1 | gel forming promoter | 25.42 |
| D-mannitol-2 | surface modifier | 12 |
| polyethylene oxide | gel forming polymer | 80 |
| sodium stearyl fumarate | lubricant | 1.2 |
| Total | | 120 |

Example 3

In a fluid bed dryer granulator (MP-01, POWREX), and according to the formulation of Table 3, pioglitazone hydrochloride (fine pulverized product, average particle size about 5 μm), microcrystalline cellulose, D-mannitol (in Table 3, D-mannitol-1) and polyethylene oxide (Polyox WSR-303, Dow chemical company) were uniformly mixed, and the mixture was granulated while spraying an aqueous solution of D-mannitol (in Table 3, D-mannitol-2) and dried in the granulator. The obtained granules were sieved using a 16M sieve to give a sieved powder. To the sieved powder was added sodium stearyl fumarate, and the mixture was admixed by hand in a 10 L plastic bag to give granules for tableting. The granules were tableted in weight 120 mg by a rotary tableting machine (Correct 19K, Kikusui Seisakusho Ltd.) with a 7 mmϕ punch to give 3,000 core tablets containing 1 mg of pioglitazone per tablet.

TABLE 3

| additive | function | formulation amount (mg/tablet) |
|---|---|---|
| pioglitazone hydrochloride | active ingredient | 1.1 |
| (pioglitazone free form) | | (1) |
| microcrystalline cellulose | gel forming promoter | 0.3 |
| D-mannitol-1 | gel forming promoter | 69.4 |
| D-mannitol-2 | surface modifier | 12 |
| polyethylene oxide | gel forming polymer | 36 |
| sodium stearyl fumarate | lubricant | 1.2 |
| Total | | 120 |

Example 4

In a fluid bed dryer granulator (MP-01, POWREX), and according to the formulation of Table 4, pioglitazone hydrochloride (fine pulverized product, average particle size about 5 μm), microcrystalline cellulose, D-mannitol (in Table 4, D-mannitol-1) and polyethylene oxide (Polyox WSR N12-K, Dow chemical company) were uniformly mixed, and the mixture was granulated while spraying an aqueous solution of D-mannitol (in Table 4, D-mannitol-2) and dried in the granulator. The obtained granules were sieved using a 16M sieve to give a sieved powder. To the sieved powder was added sodium stearyl fumarate, and the mixture was admixed by hand in a 10 L plastic bag to give granules for tableting. The granules were tableted in weight 120 mg by a rotary tableting machine (Correct 19K, Kikusui Seisakusho Ltd.) with a 7 mmϕ punch to give 3,000 core tablets containing 4 mg of pioglitazone per tablet.

TABLE 4

| additive | function | formulation amount (mg/tablet) |
|---|---|---|
| pioglitazone hydrochloride | active ingredient | 4.4 |
| (pioglitazone free form) | | (4) |
| microcrystalline cellulose | gel forming promoter | 1.1 |
| D-mannitol-1 | gel forming promoter | 21.3 |
| D-mannitol-2 | surface modifier | 12 |
| polyethylene oxide | gel forming polymer | 80 |
| sodium stearyl fumarate | lubricant | 1.2 |
| Total | | 120 |

Example 5

In a fluid bed dryer granulator (MP-01, POWREX), and according to the formulation of Table 5, pioglitazone hydrochloride (fine pulverized product, average particle size about 5 μm), microcrystalline cellulose, D-mannitol-1 (in Table 5, D-mannitol-1) and polyethylene oxide (Polyox WSR-303, Dow chemical company) were uniformly mixed, and the mixture was granulated while spraying an aqueous solution of D-mannitol (in Table 5, D-mannitol-2) and dried in the granulator. The obtained granules were sieved using a 16M sieve to give a sieved powder. To the sieved powder was added sodium stearyl fumarate, and the mixture was admixed by hand in a 10 L plastic bag to give granules for tableting. The granules were tableted in weight 120 mg by a rotary tableting machine (Correct 19K, Kikusui Seisakusho Ltd.) with a 7 mmϕ punch to give 3,000 core tablets containing 4 mg of pioglitazone per tablet.

TABLE 5

| additive | function | formulation amount (mg/tablet) |
|---|---|---|
| pioglitazone hydrochloride | active ingredient | 4.4 |
| (pioglitazone free form) | | (4) |
| microcrystalline cellulose | gel forming promoter | 1.1 |
| D-mannitol-1 | gel forming promoter | 71.3 |
| D-mannitol-2 | surface modifier | 6 |
| polyethylene oxide | gel forming polymer | 36 |
| sodium stearyl fumarate | lubricant | 1.2 |
| Total | | 120 |

Example 6

In a fluid bed dryer granulator (GPCG1, Glatt), and according to the formulation of Table 6, D-mannitol (in Table 6, D-mannitol-1) and polyethylene oxide (Polyox WSR N-12K, Dow chemical company) were uniformly mixed, and the mixture was granulated while spraying an aqueous solution of D-mannitol (in Table 6, D-mannitol-2) and dried in the granulator. The obtained granules were sieved using a 16M sieve to give a sieved powder. To the sieved powder were added pioglitazone hydrochloride (fine pulverized product, average particle size about 5 μm), microcrystalline cellulose and sodium stearyl fumarate, and they were mixed in a V-type mixer (4 Quart V-Shell Blender, GlobePharma) to give granules for tableting. The granules were tableted in weight 120 mg by a rotary tableting machine (Minipress, GlobePharma) with a 7 mmϕ punch to give 3,000 core tablets containing 4 mg of pioglitazone per tablet.

TABLE 6

| additive | function | formulation amount (mg/tablet) |
|---|---|---|
| pioglitazone hydrochloride | active ingredient | 4.4 |
| (pioglitazone free form) | | (4) |
| microcrystalline cellulose | gel forming promoter | 1.1 |
| D-mannitol-1 | gel forming promoter | 65.3 |
| D-mannitol-2 | surface modifier | 12 |
| polyethylene oxide | gel forming polymer | 36 |
| sodium stearyl fumarate | lubricant | 1.2 |
| Total | | 120 |

Example 7

In a fluid bed dryer granulator (GPCG1, Glatt), and according to the formulation of Table 7, D-mannitol (in Table 7, D-mannitol-1) and polyethylene oxide (Polyox WSR N-12K, Dow chemical company) were uniformly mixed, and the mixture was granulated while spraying an aqueous solution of D-mannitol (in Table 7, D-mannitol-2) and dried in the granulator. The obtained granules were sieved by Comil (Quadro Comil, POWREX) to give a sieved powder. To the sieved powder were added pioglitazone hydrochloride (fine pulverized product, average particle size about 5 μm), microcrystalline cellulose and sodium stearyl fumarate, and they were mixed in a V-type mixer (4 Quart V-Shell Blender, GlobePharma) to give granules for tableting. The granules were tableted in weight 120 mg by a rotary tableting machine (Minipress, GlobePharma) with a 7 mmϕ punch to give 3,000 core tablets containing 4 mg of pioglitazone per tablet.

TABLE 7

| additive | function | formulation amount (mg/tablet) |
| --- | --- | --- |
| pioglitazone hydrochloride | active ingredient | 4.4 |
| (pioglitazone free form) | | (4) |
| microcrystalline cellulose | gel forming promoter | 1.1 |
| D-mannitol-1 | gel forming promoter | 21.3 |
| D-mannitol-2 | surface modifier | 12 |
| polyethylene oxide | gel forming polymer | 80 |
| sodium stearyl fumarate | lubricant | 1.2 |
| | Total | 120 |

Example 8

In a fluid bed dryer granulator (GPCG1, Glatt), and according to the formulation of Table 8, D-mannitol (in Table 8, D-mannitol-1) and polyethylene oxide (Polyox WSR-303, Dow chemical company) were uniformly mixed, and the mixture was granulated while spraying an aqueous solution of D-mannitol (in Table 8, D-mannitol-2) and dried in the granulator. The obtained granules were sieved using a 16M sieve to give a sieved powder. To the sieved powder were added pioglitazone hydrochloride (fine pulverized product, average particle size about 5 μm), microcrystalline cellulose and sodium stearyl fumarate, and they were mixed in a V-type mixer (4 Quart V-Shell Blender, GlobePharma) to give granules for tableting. The granules were tableted in weight 120 mg by a rotary tableting machine (Minipress, GlobePharma) with a 7 mmϕ punch to give 3,000 core tablets containing 4 mg of pioglitazone per tablet.

TABLE 8

| additive | function | formulation amount (mg/tablet) |
| --- | --- | --- |
| pioglitazone hydrochloride | active ingredient | 4.4 |
| (pioglitazone free form) | | (4) |
| microcrystalline cellulose | gel forming promoter | 1.1 |
| D-mannitol-1 | gel forming promoter | 65.3 |
| D-mannitol-2 | surface modifier | 12 |

TABLE 8-continued

| additive | function | formulation amount (mg/tablet) |
| --- | --- | --- |
| polyethylene oxide | gel forming polymer | 36 |
| sodium stearyl fumarate | lubricant | 1.2 |
| | Total | 120 |

Example 9

In a fluid bed dryer granulator (MP-01, POWREX), and according to the formulation of Table 9, D-mannitol (in Table 9, D-mannitol-1) and polyethylene oxide (Polyox WSR N-12K, Dow chemical company) were uniformly mixed, and the mixture was granulated while spraying an aqueous solution of D-mannitol (in Table 9, D-mannitol-2) and dried in the granulator. The obtained granules were sieved using a 16M sieve to give a sieved powder. To the sieved powder were added pioglitazone hydrochloride (fine pulverized product, average particle size about 5 μm), microcrystalline cellulose and sodium stearyl fumarate, and the mixture was admixed by hand in a 10 L plastic bag to give granules for tableting. The granules were tableted in weight 120 mg by a rotary tableting machine (Correct 19K, Kikusui Seisakusho Ltd.) with a 7 mmϕ punch to give 3,000 core tablets containing 1 mg of pioglitazone per tablet.

TABLE 9

| additive | function | formulation amount (mg/tablet) |
| --- | --- | --- |
| pioglitazone hydrochloride | active ingredient | 1.1 |
| (pioglitazone free form) | | (1.0) |
| microcrystalline cellulose | gel forming promoter | 0.3 |
| D-mannitol-1 | gel forming promoter | 25.4 |
| D-mannitol-2 | surface modifier | 12 |
| polyethylene oxide | gel forming polymer | 80 |
| sodium stearyl fumarate | lubricant | 1.2 |
| | Total | 120 |

Comparative Example 1

In a fluid bed dryer granulator (MP-01, POWREX), and according to the formulation of Table 10, pioglitazone hydrochloride (pulverized product, average particle size about 15 μm) and lactose were uniformly mixed, and the mixture was granulated while spraying an aqueous solution of hydroxypropylcellulose and dried in the granulator. The obtained granules were sieved using a 16M sieve to give a sieved powder. To the sieved powder were added carmellose calcium and magnesium stearate, and the mixture was admixed by hand in a 10 L plastic bag to give granules for tableting. The granules were tableted in weight 120 mg by a rotary tableting machine (Correct 19K, Kikusui Seisakusho Ltd.) with a 7 mmϕ punch to give 3,000 core tablets containing 1 mg of pioglitazone per tablet.

TABLE 10

| additive | function | formulation amount (mg/tablet) |
|---|---|---|
| pioglitazone hydrochloride | active ingredient | 1.1 |
| (pioglitazone free form) | | (1) |
| lactose | excipient | 108.3 |
| hydroxypropylcellulose | binder | 3 |
| carmellose calcium | disintegrant | 7.2 |
| magnesium stearate | lubricant | 0.4 |
| Total | | 120 |

Experimental Example 1

The dissolution property of the tablets obtained in Examples 1, 2 and 3 was measured. One tablet was placed in 900 mL of pH 2.0 KCl/HCl buffer, and evaluation was performed by the Paddle Method (USP, hereinafter the same), at 50 rpm, 37° C. After placing the tablet, the dissolution medium was sampled over time, filtered with a non-aqueous filter (0.45 µm), quantified by high-performance liquid column chromatography (HPLC) method under the following conditions, and the dissolution rate was calculated. The results are shown in FIG. 1.

HPLC Conditions detector: ultraviolet absorption spectrophotometer, measurement wavelength: 269 nm column: CAPCELLPAK C18 AQ, 5 µm, inner diameter: 4.6 mm, length: 50 mm (manufactured by Shiseido Co., Ltd.)

column temperature: 25° C.

mobile phase: acetonitrile:0.1 mol/L ammonium acetate buffer:glacial acetic acid mixed solution (25:25:1)

flow: 0.7 mL/min

Experimental Example 2

Figure 2:
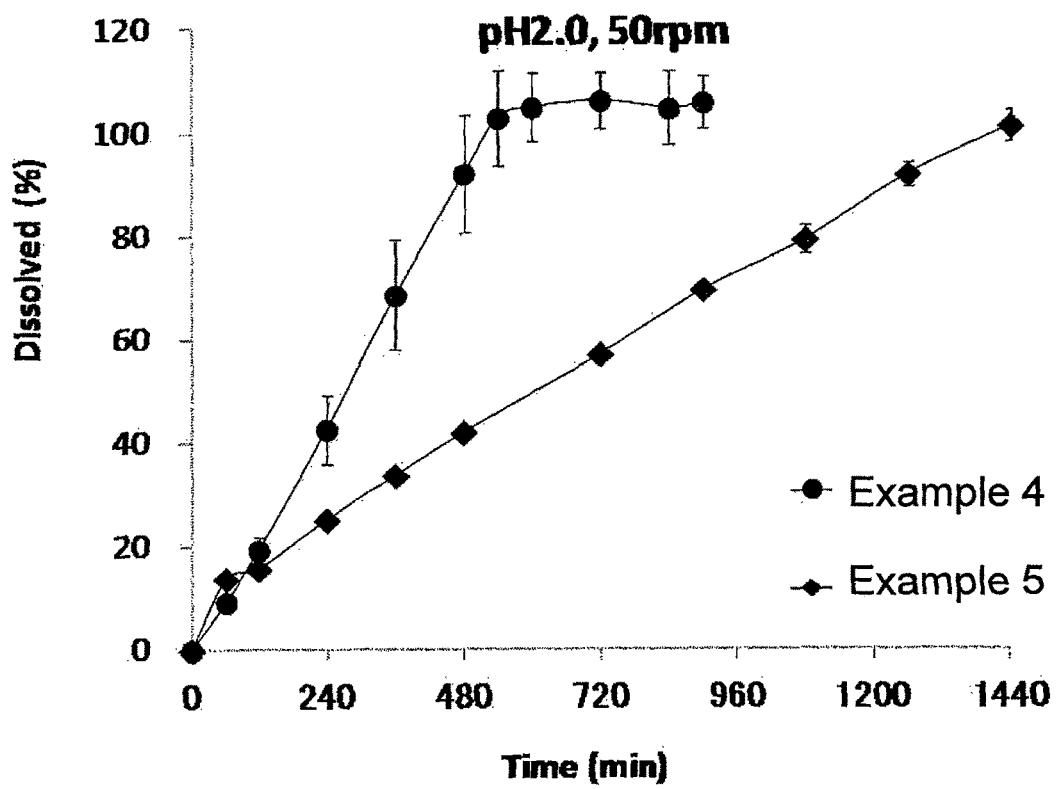
FIG. 2 shows the results in Experimental Example 2.

The dissolution property of the tablets obtained in Examples 4 and 5 was measured. One tablet was placed in 900 mL of pH2.0 KCl/HCl buffer, and evaluation was performed by the Paddle Method (USP), at 50 rpm, 37° C. After placing the tablet, the dissolution medium was sampled over time, filtered with a non-aqueous filter (0.45 µm), quantified by high-performance liquid column chromatography (HPLC) method under the conditions similar to those in Experimental Example 1, and the dissolution rate was calculated. The results are shown in FIG. 2.

Experimental Example 3

Figure 3:
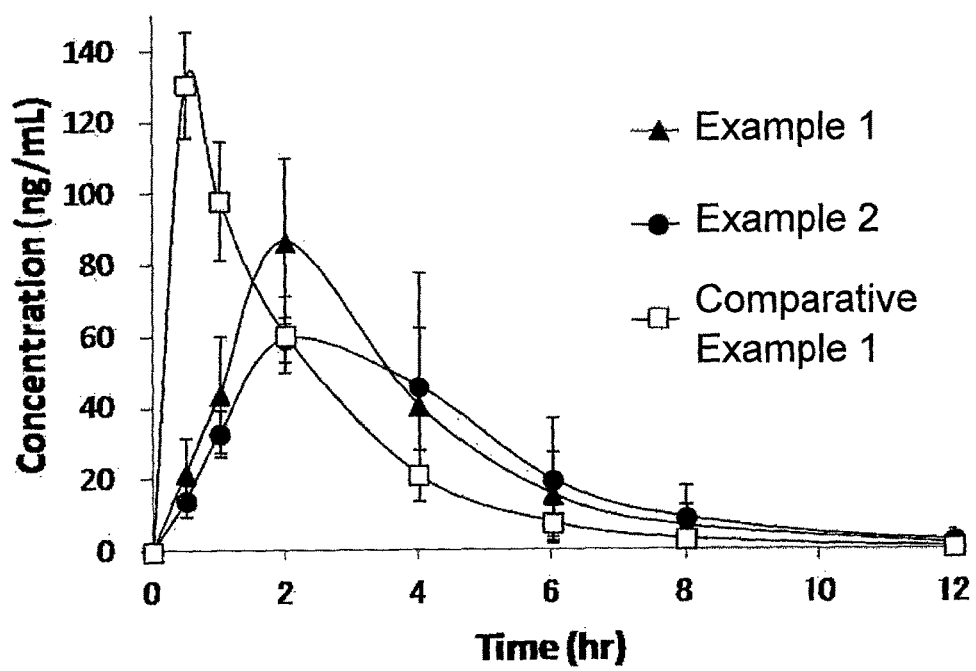
FIG. 3 shows the results in Experimental Example 3.

The pharmacokinetics after oral administration under fasting conditions of the tablets obtained in Examples 1, 2 and Comparative Example 1 to pentagastrin-treated beagle was measured. The plasma concentration was measured before administration, and 0.5 hr, 1 hr, 2 hr, 4 hr, 6 hr, 8 hr and 12 hr after administration, and the area under plasma concentration-time curve (AUC) was calculated by the trapezoid formula. The results are shown in FIG. 3 and Table 11.

TABLE 11

| | Dose (mg/head) | $T_{max}$ (hr) | $C_{max}$ (ng/mL) | $AUC_{0-12\ hr}$ (ng min/mL) |
|---|---|---|---|---|
| Example 1 | 1 | 2.0 (0) | 86.7 (23.1) | 319.7 (141.5) |
| Example 2 | 1 | 2.4 (0.9) | 67.9 (19.4) | 304.1 (148.9) |
| Comparative Example 1 | 1 | 0.5 (0) | 131.0 (14.8) | 304.2 (53.7) |

In the Table, the numerical values in the parentheses show standard deviation.

Experimental Example 4

Figure 4:
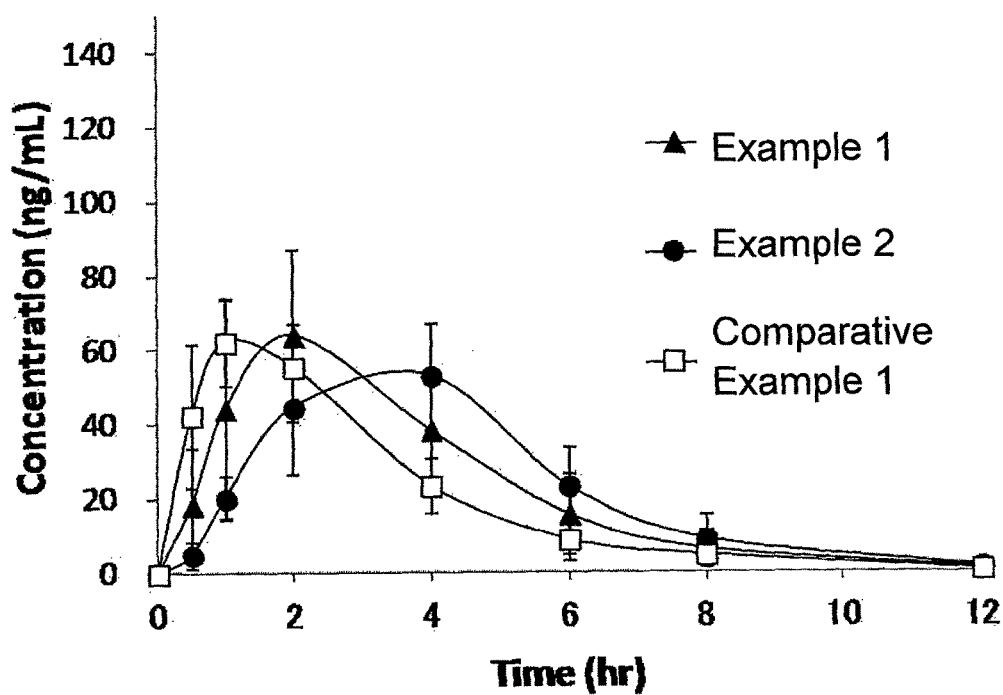
FIG. 4 shows the results in Experimental Example 4.

The pharmacokinetics after oral administration under food ingestion conditions of the tablets obtained in Examples 1, 2 and Comparative Example 1 to beagle was measured. The plasma concentration was measured before administration, and 0.5 hr, 1 hr, 2 hr, 4 hr, 6 hr, 8 hr and 12 hr after administration, and the area under plasma concentration-time curve (AUC) was calculated by the trapezoid formula. The results are shown in FIG. 4 and Table 12.

TABLE 12

| | Dose (mg/head) | $T_{max}$ (hr) | $C_{max}$ (ng/mL) | $AUC_{0-12\ hr}$ (ng min/mL) |
|---|---|---|---|---|
| Example 1 | 1 | 2.2 (1.1) | 70.1 (16.6) | 275.7 (81.6) |
| Example 2 | 1 | 3.2 (1.1) | 55.9 (11.8) | 277.3 (95.8) |
| Comparative Example 1 | 1 | 1.4 (0.5) | 62.6 (11.8) | 236.6 (56.9) |

In the Table, the numerical values in the parentheses show standard deviation.

Experimental Example 5

Figure 5:
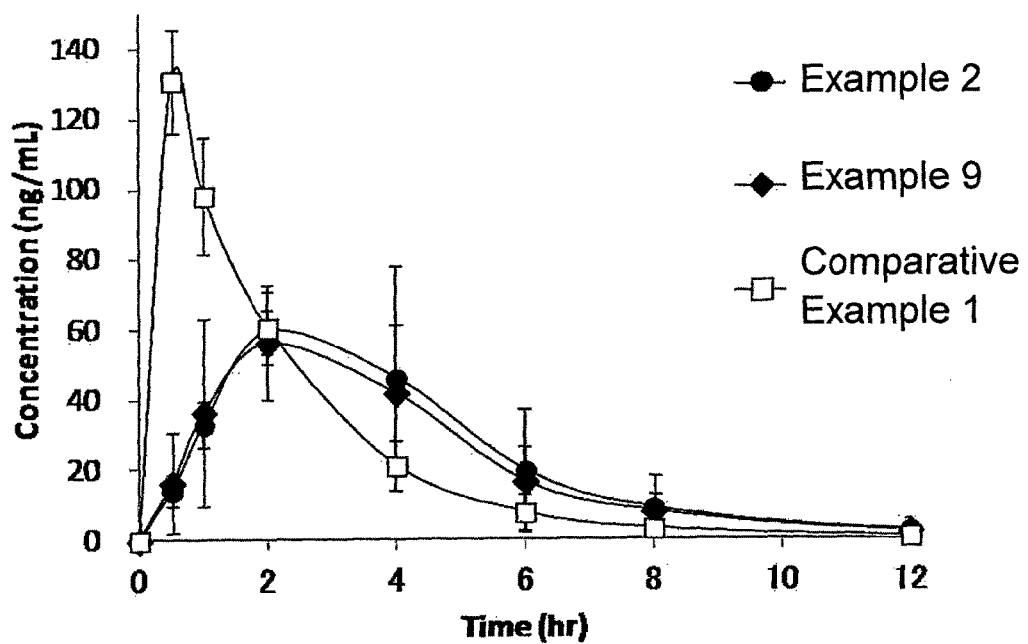
FIG. 5 shows the results in Experimental Example 5.

The pharmacokinetics after oral administration under fasting conditions of the tablets obtained in Examples 2, 9 and Comparative Example 1 to pentagastrin-treated beagle was measured. The plasma concentration was measured before administration, and 0.5 hr, 1 hr, 2 hr, 4 hr, 6 hr, 8 hr and 12 hr after administration, and the area under plasma concentration-time curve (AUC) was calculated by the trapezoid formula. The results are shown in FIG. 5 and Table 13.

TABLE 13

| | Dose (mg/head) | $T_{max}$ (hr) | $C_{max}$ (ng/mL) | $AUC_{0-12\ hr}$ (ng min/mL) |
|---|---|---|---|---|
| Example 2 | 1 | 2.4 (0.9) | 67.9 (19.4) | 304.1 (148.9) |
| Example 9 | 1 | 2.2 (1.1) | 58.0 (16.6) | 285.0 (124.0) |
| Comparative Example 1 | 1 | 0.5 (0) | 131.0 (14.8) | 304.2 (53.7) |

In the Table, the numerical values in the parentheses show standard deviation.

Example 10

In a fluid bed dryer granulator (CPCG1, Glatt), and according to the formulation of Table 14, pioglitazone hydrochloride (fine pulverized product, average particle size about 5 µm), microcrystalline cellulose, D-mannitol (in Table 14, D-mannitol-1) and polyethylene oxide (Polyox WSR N12-K, Dow chemical company) were uniformly mixed, and the mixture was granulated while spraying an aqueous solution of D-mannitol (in Table 14, D-mannitol-2) and dried in the granulator. The obtained granules were sieved using a 20M sieve to give a sieved powder. To the sieved powder was added sodium stearyl fumarate, and they were mixed in a V-type mixer (4 Quart V-Shell Blender, GlobePharma) at 25 rpm for 3 min to give granules for tableting. The granules were tableted in weight 120 mg by a rotary tableting machine (Minipress, GlobePharma) with a 7 mmϕ punch to give 4,000 core tablets containing 4 mg of pioglitazone per tablet.

TABLE 14

| additive | function | formulation amount (mg/tablet) |
| --- | --- | --- |
| pioglitazone hydrochloride (pioglitazone free form) | active ingredient | 4.42 (4) |
| microcrystalline cellulose | gel forming promoter | 1.1 |
| D-mannitol-1 | gel forming promoter | 65.28 |
| D-mannitol-2 | surface modifier | 12 |
| polyethylene oxide | gel forming polymer | 36 |
| sodium stearyl fumarate | lubricant | 1.2 |
| Total | | 120 |

Example 11

In a fluid bed dryer granulator (CPCG1, Glatt), and according to the formulation of Table 15, pioglitazone hydrochloride (fine pulverized product, average particle size about 5 μm), microcrystalline cellulose, D-mannitol (in Table 15, D-mannitol-1) and polyethylene oxide (Polyox WSR N12-K, Dow chemical company) were uniformly mixed, and the mixture was granulated while spraying an aqueous solution of D-mannitol (in Table 15, D-mannitol-2) and dried in the granulator. The obtained granules were sieved using a 20M sieve to give a sieved powder. To the sieved powder was added sodium stearyl fumarate, and they were mixed in a V-type mixer (4 Quart V-Shell Blender, GlobePharma) at 25 rpm for 3 min to give granules for tableting. The granules were tableted in weight 120 mg by a rotary tableting machine (Minipress, GlobePharma) with a 7 mmϕ punch to give 4,000 core tablets containing 4 mg of pioglitazone per tablet.

TABLE 15

| additive | function | formulation amount (mg/tablet) |
| --- | --- | --- |
| pioglitazone hydrochloride (pioglitazone free form) | active ingredient | 4.42 (4) |
| microcrystalline cellulose | gel forming promoter | 1.1 |
| D-mannitol-1 | gel forming promoter | 21.28 |
| D-mannitol-2 | surface modifier | 12 |
| polyethylene oxide | gel forming polymer | 80 |
| sodium stearyl fumarate | lubricant | 1.2 |
| Total | | 120 |

Example 12

In a fluid bed dryer granulator (CPCG1, Glatt), and according to the formulation of Table 16, pioglitazone hydrochloride (fine pulverized product, average particle size about 5 μm), microcrystalline cellulose, D-mannitol (in Table 16, D-mannitol-1) and polyethylene oxide (Polyox WSR 303, Dow chemical company) were uniformly mixed, and the mixture was granulated while spraying an aqueous solution of D-mannitol (in Table 16, D-mannitol-2) and dried in the granulator. The obtained granules were sieved using a 20M sieve to give a sieved powder. To the sieved powder was added sodium stearyl fumarate, and they were mixed in a V-type mixer (4 Quart V-Shell Blender, GlobePharma) at 25 rpm for 3 min to give granules for tableting. The granules were tableted in weight 120 mg by a rotary tableting machine (Minipress, GlobePharma) with a 7 mmϕ punch to give 4,000 core tablets containing 4 mg of pioglitazone per tablet.

TABLE 16

| additive | function | formulation amount (mg/tablet) |
| --- | --- | --- |
| pioglitazone hydrochloride (pioglitazone free form) | active ingredient | 4.42 (4) |
| microcrystalline cellulose | gel forming promoter | 1.1 |
| D-mannitol-1 | gel forming promoter | 65.28 |
| D-mannitol-2 | surface modifier | 12 |
| polyethylene oxide | gel forming polymer | 36 |
| sodium stearyl fumarate | lubricant | 1.2 |
| Total | | 120 |

Reference Example 1

According to the formulation of Table 17, pioglitazone hydrochloride and citric acid were dissolved in purified water to give a solution for the test.

TABLE 17

| additive | function | formulation amount (mg/solution) |
| --- | --- | --- |
| pioglitazone hydrochloride (pioglitazone free form) | active ingredient | 4.42 (4) |
| citric acid | solubilizing agents | 267.9 |
| purified water | solvent | q.s. |
| Total | | 13.4 mL |

Example 13

In a fluid bed dryer granulator (LAB-1, POWREX), and according to the formulation of Table 18, pioglitazone hydrochloride (fine pulverized product, average particle size about 5 μm), microcrystalline cellulose, D-mannitol (in Table 18, D-mannitol-1) and polyethylene oxide (Polyox WSR N12-K, Dow chemical company) were uniformly mixed, and the mixture was granulated while spraying a dispersion obtained by dissolving D-mannitol (in Table 18, D-mannitol-2) and hydroxypropylcellulose in water, and dispersing red ferric oxide and yellow ferric oxide therein and dried in the granulator. The obtained granules were sieved using a 16M sieve to give a sieved powder. To the sieved powder were added sodium stearyl fumarate and butylhydroxyanisole, and the mixture was admixed by hand in a 10 L plastic bag to give granules for tableting. The granules were measured by weight 120 mg and tableted by Autograph (AG-1, Shimadzu Corporation) with a 8.5 mm×5 mm oval punch to give 20 core tablets containing 0.1 mg of pioglitazone per tablet.

TABLE 18

| additive | function | formulation amount (mg/tablet) |
|---|---|---|
| pioglitazone hydrochloride | active | 0.11 |
| (pioglitazone free form) | ingredient | (0.1) |
| microcrystalline cellulose | gel forming promoter | 0.028 |
| D-mannitol-1 | gel forming promoter | 66.702 |
| D-mannitol-2 | surface modifier | 12 |
| hydroxypropylcellulose | binder | 3.6 |
| red ferric oxide | colorant | 0.12 |
| yellow ferric oxide | colorant | 0.12 |
| butylhydroxyanisole | antioxidant | 0.12 |
| polyethylene oxide | gel forming polymer | 36 |
| sodium stearyl fumarate | lubricant | 1.2 |
| Total | | 120 |

Example 14

In a fluid bed dryer granulator (LAB-1, POWREX), and according to the formulation of Table 19, pioglitazone hydrochloride (fine pulverized product, average particle size about 5 μm), microcrystalline cellulose, D-mannitol (in Table 19, D-mannitol-1) and polyethylene oxide (Polyox WSR N12-K, Dow chemical company) were uniformly mixed, and the mixture was granulated while spraying a dispersion obtained by dissolving D-mannitol (in Table 19, D-mannitol-2) and hydroxypropylcellulose in water, and dispersing red ferric oxide and yellow ferric oxide therein and dried in the granulator. The obtained granules were sieved using a 16M sieve to give a sieved powder. To the sieved powder were added sodium stearyl fumarate and butylhydroxyanisole, and the mixture was admixed by hand in a 10 L plastic bag to give granules for tableting. The granules were measured by weight 120 mg and tableted by Autograph (AG-1, Shimadzu Corporation) with a 8.5 mm×5 mm oval punch to give 20 core tablets containing 0.3 mg of pioglitazone per tablet.

TABLE 19

| additive | function | formulation amount (mg/tablet) |
|---|---|---|
| pioglitazone hydrochloride | active | 0.33 |
| (pioglitazone free form) | ingredient | (0.3) |
| microcrystalline cellulose | gel forming promoter | 0.083 |
| D-mannitol-1 | gel forming promoter | 66.427 |
| D-mannitol-2 | surface modifier | 12 |
| hydroxypropylcellulose | binder | 3.6 |
| red ferric oxide | colorant | 0.12 |
| yellow ferric oxide | colorant | 0.12 |
| butylhydroxyanisole | antioxidant | 0.12 |
| polyethylene oxide | gel forming polymer | 36 |
| sodium stearyl fumarate | lubricant | 1.2 |
| Total | | 120 |

Example 15

In a fluid bed dryer granulator (WSG-60, POWREX), and according to the formulation of Table 20, pioglitazone hydrochloride (fine pulverized product, average particle size about 5 μcm), microcrystalline cellulose, D-mannitol (in Table 20, D-mannitol-1) and polyethylene oxide (Polyox WSR N12-K, Dow chemical company) were uniformly mixed, and the mixture was granulated while spraying a dispersion obtained by dissolving D-mannitol (in Table 20, D-mannitol-2) and hydroxypropylcellulose in water, and dispersing red ferric oxide and yellow ferric oxide therein and dried in the granulator. The obtained granules were sieved using a power mill (P-7S, SHOWA KAGAKU KIKAI CO., LTD.) to give a sieved powder. To the sieved powder were added sodium stearyl fumarate and butylhydroxyanisole and they were mixed in a tumbler mixer (TM-400S, SHOWA KAGAKU KIKAI CO., LTD.) at 11 rpm for 2 min to give granules for tableting. The granules were tableted in weight 120 mg by a rotary tableting machine (AQUARIUS 36K, Kikusui Seisakusho Ltd.) with a 8.5 mm×5 mm oval punch to give 1,000,000 core tablets containing 0.8 mg of pioglitazone per tablet.

TABLE 20

| additive | function | formulation amount (mg/tablet) |
|---|---|---|
| pioglitazone hydrochloride | active | 0.88 |
| (pioglitazone free form) | ingredient | (0.8) |
| microcrystalline cellulose | gel forming promoter | 0.22 |
| D-mannitol-1 | gel forming promoter | 65.74 |
| D-mannitol-2 | surface modifier | 12 |
| hydroxypropylcellulose | binder | 3.6 |
| red ferric oxide | colorant | 0.12 |
| yellow ferric oxide | colorant | 0.12 |
| butylhydroxyanisole | antioxidant | 0.12 |
| polyethylene oxide | gel forming polymer | 36 |
| sodium stearyl fumarate | lubricant | 1.2 |
| Total | | 120 |

Example 16

In a fluid bed dryer granulator (WSG-60, POWREX), and according to the formulation of Table 21, pioglitazone hydrochloride (fine pulverized product, average particle size about 5 μm), microcrystalline cellulose, D-mannitol (in Table 21, D-mannitol-1) and polyethylene oxide (Polyox WSR N12-K, Dow chemical company) were uniformly mixed, and the mixture was granulated while spraying a dispersion obtained by dissolving D-mannitol (in Table 21, D-mannitol-2) and hydroxypropylcellulose in water, and dispersing red ferric oxide and yellow ferric oxide therein and dried in the granulator. The obtained granules were sieved using a power mill (P-7S, SHOWA KAGAKU KIKAI CO., LTD.) to give a sieved powder. To the sieved powder were added sodium stearyl fumarate and butylhydroxyanisole and they were mixed in a tumbler mixer (TM-400S, SHOWA KAGAKU KIKAI CO., LTD.) at 11 rpm for 2 min to give granules for tableting. The granules were tableted in weight 120 mg by a rotary tableting machine (AQUARIUS 36K, Kikusui Seisakusho Ltd.) with a 8.5 mm×5 mm oval punch to give 1,000,000 core tablets containing 2.8 mg of pioglitazone per tablet.

TABLE 21

| additive | function | formulation amount (mg/tablet) |
| --- | --- | --- |
| pioglitazone hydrochloride | active | 3.09 |
| (pioglitazone free form) | ingredient | (2.8) |
| microcrystalline cellulose | gel forming promoter | 0.77 |
| D-mannitol-1 | gel forming promoter | 62.98 |
| D-mannitol-2 | surface modifier | 12 |
| hydroxypropylcellulose | binder | 3.6 |
| red ferric oxide | colorant | 0.12 |
| yellow ferric oxide | colorant | 0.12 |
| butylhydroxyanisole | antioxidant | 0.12 |
| polyethylene oxide | gel forming polymer | 36 |
| sodium stearyl fumarate | lubricant | 1.2 |
| Total | | 120 |

Example 17

In a fluid bed dryer granulator (WSG-60, POWREX), and according to the formulation of Table 22, pioglitazone hydrochloride (fine pulverized product, average particle size about 5 μm), microcrystalline cellulose, D-mannitol (in Table 22, D-mannitol-1) and polyethylene oxide (Polyox WSR N12-K, Dow chemical company) were uniformly mixed, and the mixture was granulated while spraying a dispersion obtained by dissolving D-mannitol (in Table 22, D-mannitol-2) and hydroxypropylcellulose in water, and dispersing red ferric oxide and yellow ferric oxide therein and dried in the granulator. The obtained granules were sieved using a power mill (P-7S, SHOWA KAGAKU KIKAI CO., LTD.) to give a sieved powder. To the sieved powder were added sodium stearyl fumarate and butylhydroxyanisole and they were mixed in a tumbler mixer (TM-400S, SHOWA KAGAKU KIKAI CO., LTD.) at 11 rpm for 2 min to give granules for tableting. The granules were tableted in weight 120 mg by a rotary tableting machine (AQUARIUS 36K, Kikusui Seisakusho Ltd.) with a 8.5 mm×5 mm oval punch to give 1,000,000 core tablets containing 5.2 mg of pioglitazone per tablet.

TABLE 22

| additive | function | formulation amount (mg/tablet) |
| --- | --- | --- |
| pioglitazone hydrochloride | active | 5.73 |
| (pioglitazone free form) | ingredient | (5.2) |
| microcrystalline cellulose | gel forming promoter | 1.43 |
| D-mannitol-1 | gel forming promoter | 59.68 |
| D-mannitol-2 | surface modifier | 12 |
| hydroxypropylcellulose | binder | 3.6 |
| red ferric oxide | colorant | 0.12 |
| yellow ferric oxide | colorant | 0.12 |
| butylhydroxyanisole | antioxidant | 0.12 |
| polyethylene oxide | gel forming polymer | 36 |
| sodium stearyl fumarate | lubricant | 1.2 |
| Total | | 120 |

Experimental Example 6

The pharmacokinetics of pioglitazone after oral administration of the tablet obtained in Example 10 to human under fasting conditions was measured. The plasma concentration before administration and 0.5 hr, 1 hr, 1.5 hr, 2 hr, 3 hr, 4 hr, 6 hr, 8 hr, 10 hr, 12 hr, 24 hr, 36 hr and 48 hr after administration was measured, and the area under plasma concentration-time curve (AUC) was calculated by the trapezoid formula. The results are shown in Table 23.

TABLE 23

| preparation | Tmax (hr) | Cmax (ng/ml) | AUC (0-tlqc) (ng · hr/ml) | AUC (0-inf) (ng · hr/ml) | T½ |
| --- | --- | --- | --- | --- | --- |
| Example 10 | 4.0 | 87.8 | 1258 | 1348 | 11.0 |

Experimental Example 7

The pharmacokinetics of pioglitazone after oral administration of the tablet obtained in Example 11 to human under fasting conditions was measured. The plasma concentration before administration and 0.5 hr, 1 hr, 1.5 hr, 2 hr, 3 hr, 4 hr, 6 hr, 8 hr, 10 hr, 12 hr, 24 hr, 36 hr and 48 hr after administration was measured, and the area under plasma concentration-time curve (AUC) was calculated by the trapezoid formula. The results are shown in Table 24.

TABLE 24

| preparation | Tmax (hr) | Cmax (ng/ml) | AUC (0-tlqc) (ng · hr/ml) | AUC (0-inf) (ng · hr/ml) | T½ |
| --- | --- | --- | --- | --- | --- |
| Example 11 | 4.0 | 46.2 | 889 | 1053 | 16.9 |

Experimental Example 8

The pharmacokinetics of pioglitazone after oral administration of the tablet obtained in Example 12 to human under fasting conditions was measured. The plasma concentration before administration and 0.5 hr, 1 hr, 1.5 hr, 2 hr, 3 hr, 4 hr, 6 hr, 8 hr, 10 hr, 12 hr, 24 hr, 36 hr and 48 hr after administration was measured, and the area under plasma concentration-time curve (AUC) was calculated by the trapezoid formula. The results are shown in Table 25.

TABLE 25

| preparation | Tmax (hr) | Cmax (ng/ml) | AUC (0-tlqc) (ng · hr/ml) | AUC (0-inf) (ng · hr/ml) | T½ |
| --- | --- | --- | --- | --- | --- |
| Example 12 | 5.0 | 34.1 | 805 | 908 | 13.2 |

Experimental Example 9

The pharmacokinetics of pioglitazone after oral administration of the solution obtained in Reference Example 1 to human under fasting conditions was measured. The plasma concentration before administration and 0.5 hr, 1 hr, 1.5 hr, 2 hr, 3 hr, 4 hr, 6 hr, 8 hr, 10 hr, 12 hr, 24 hr, 36 hr and 48 hr after administration was measured, and the area under plasma concentration-time curve (AUC) was calculated by the trapezoid formula. The results are shown in Table 26.

TABLE 26

| preparation | Tmax (hr) | Cmax (ng/ml) | AUC (0-tlqc) (ng · hr/ml) | AUC (0-inf) (ng · hr/ml) | T½ |
|---|---|---|---|---|---|
| Reference Example 1 | 1.0 | 227.7 | 1632 | 1652 | 5.2 |

Experimental Example 10

Figure 6:
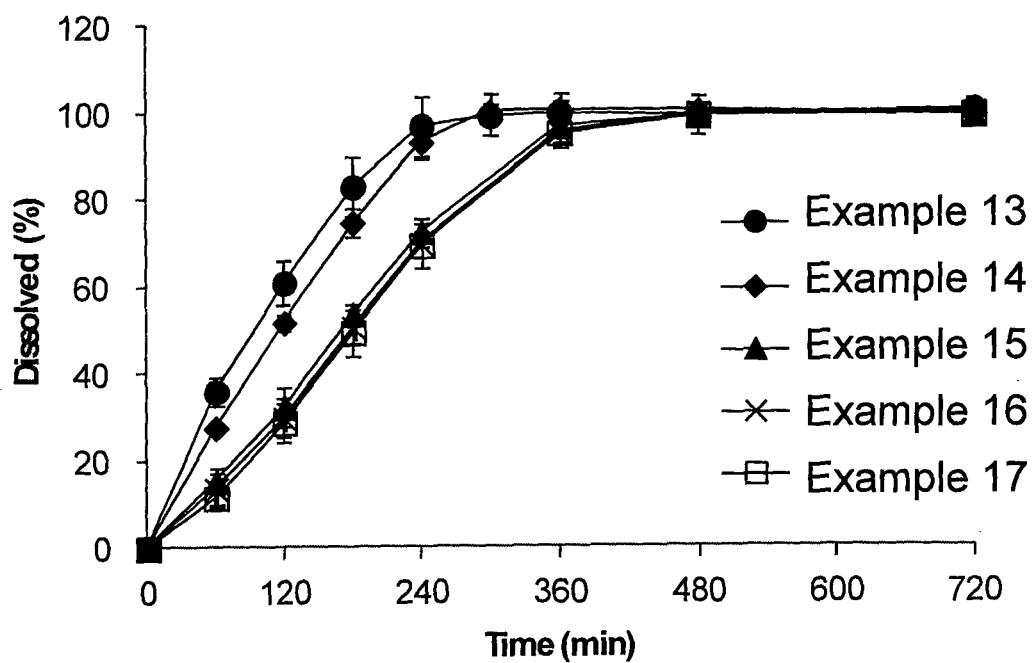
FIG. 6 shows the results in Experimental Example 10.

The dissolution property of the tablets obtained in Examples 13, 14, 15, 16 and 17 was measured. One tablet each of Examples 13 and 14 was placed in 900 mL of HCl buffer (pH 2.0, 37° C.), and evaluation was performed by the USP Paddle Method at 50 rpm. One tablet each of Examples 15, 16 and 17 was placed in 900 mL of phosphate buffer (pH 6.8, 0.1% CTAB, 37° C.), and evaluation was performed by the USP Paddle Method at 50 rpm. After placing the tablet, the dissolution medium was sampled over time, filtered with a non-aqueous filter (0.45 μm), quantified by high-performance liquid column chromatography (HPLC) method under the same conditions as those in Experimental Example 1 except that "YMC-PACK ODS-A, S-5, 12 nm, inner diameter: 4.6 mm, length: 75 mm (manufactured by YMC CO., LTD.)" was used as the column instead of "CAPCELL-PAK C18 AQ, 5 μm, inner diameter: 4.6 mm, length: 50 mm (manufactured by Shiseido Co., Ltd.)", and the dissolution rate was calculated. The results are shown in FIG. 6.

Examples 18-39

In a mortar and according to the formulations of Tables 27-1, 27-2, pioglitazone hydrochloride (fine pulverized product, average particle size about 5 μm), microcrystalline cellulose, D-mannitol and polyethylene oxide (Polyox various viscosity grades, Dow chemical company) were uniformly mixed, sodium stearyl fumarate was added, and the mixture was uniformly mixed to give granules for tableting. The granules were measured by weight 120 mg and tableted by Autograph (AG-1, Shimadzu Corporation) with a 7 mmφ punch to give 20 core tablets containing 1 mg of pioglitazone per tablet.

Examples 40-41

In a fluid bed dryer granulator (MP-01, POWREX), and according to the formulation of Table 28, pioglitazone hydrochloride (fine pulverized product, average particle size about 5 μm), microcrystalline cellulose, D-mannitol (in Table 28, D-mannitol-1) and polyethylene oxide (Polyox various viscosity grades, Dow chemical company) were uniformly mixed, and the mixture was granulated while spraying an aqueous solution of D-mannitol (in Table 28, D-mannitol-2) and hydroxypropylcellulose (added in Example 41 alone) and dried in the granulator. The obtained granules were sieved using a 16M sieve to give a sieved powder. To the sieved powder was added sodium stearyl fumarate, and the mixture was admixed by hand in a 10 L plastic bag to give granules for tableting. The granules were measured by weight 120 mg and tableted by Autograph (AG-1, Shimadzu Corporation) with a 7 mmφ punch to give 20 core tablets containing 1 mg of pioglitazone per tablet.

TABLE 27-1

| additive | function | Example (mg/tablet) | | | | | | | | | | | |
|---|---|---|---|---|---|---|---|---|---|---|---|---|
| | | 18 | 19 | 20 | 21 | 22 | 23 | 24 | 25 | 26 | 27 | 28 | 29 |
| polyethylene oxide WSR N-750 | gel forming polymer | 84 | 96 | 108 | — | — | — | — | — | — | — | — | — |
| polyethylene oxide WSR 205 | gel forming polymer | — | — | — | 48 | 60 | 84 | — | — | — | — | — | — |
| polyethylene oxide WSR 1105 | gel forming polymer | — | — | — | — | — | — | 36 | 48 | 72 | — | — | — |
| polyethylene oxide WSR N-12K | gel forming polymer | — | — | — | — | — | — | — | — | — | 30 | 36 | 42 |
| pioglitazone hydrochloride (pioglitazone free form) | active ingredient | 1.1 (1) | 1.1 (1) | 1.1 (1) | 1.1 (1) | 1.1 (1) | 1.1 (1) | 1.1 (1) | 1.1 (1) | 1.1 (1) | 1.1 (1) | 1.1 (1) | 1.1 (1) |
| microcrystalline cellulose | gel forming promoter | 0.28 | 0.28 | 0.28 | 0.28 | 0.28 | 0.28 | 0.28 | 0.28 | 0.28 | 0.28 | 0.28 | 0.28 |
| D-mannitol | gel forming promoter | 33.42 | 21.42 | 9.42 | 69.42 | 57.42 | 33.42 | 81.42 | 69.42 | 45.42 | 87.42 | 81.42 | 75.42 |
| sodium stearyl fumarate | lubricant | 1.2 | 1.2 | 1.2 | 1.2 | 1.2 | 1.2 | 1.2 | 1.2 | 1.2 | 1.2 | 1.2 | 1.2 |
| Total | | 120 | 120 | 120 | 120 | 120 | 120 | 120 | 120 | 120 | 120 | 120 | 120 |

TABLE 27-2

| additive | function | Example (mg/tablet) | | | | | | | | | |
|---|---|---|---|---|---|---|---|---|---|---|---|
| | | 30 | 31 | 32 | 33 | 34 | 35 | 36 | 37 | 38 | 39 |
| polyethylene oxide WSR N-12K | gel forming polymer | 54 | — | — | — | — | — | — | — | — | — |
| polyethylene oxide WSR N-60K | gel forming polymer | — | 18 | 24 | 30 | 36 | 42 | — | — | — | — |
| polyethylene oxide WSR 301 | gel forming polymer | — | — | — | — | — | — | 18 | 24 | — | — |

TABLE 27-2-continued

| additive | function | 30 | 31 | 32 | 33 | 34 | 35 | 36 | 37 | 38 | 39 |
|---|---|---|---|---|---|---|---|---|---|---|---|
| polyethylene oxide WSR Coagulant | gel forming polymer | — | — | — | — | — | — | — | — | 18 | 24 |
| pioglitazone hydrochloride (pioglitazone free form) | active ingredient | 1.1 (1) | 1.1 (1) | 1.1 (1) | 1.1 (1) | 1.1 (1) | 1.1 (1) | 1.1 (1) | 1.1 (1) | 1.1 (1) | 1.1 (1) |
| microcrystalline cellulose | gel forming promoter | 0.28 | 0.28 | 0.28 | 0.28 | 0.28 | 0.28 | 0.28 | 0.28 | 0.28 | 0.28 |
| D-mannitol | gel forming promoter | 63.42 | 99.42 | 93.42 | 87.42 | 81.42 | 75.42 | 99.42 | 93.42 | 99.42 | 93.42 |
| sodium stearyl fumarate | lubricant | 1.2 | 1.2 | 1.2 | 1.2 | 1.2 | 1.2 | 1.2 | 1.2 | 1.2 | 1.2 |
| Total | | 120 | 120 | 120 | 120 | 120 | 120 | 120 | 120 | 120 | 120 |

TABLE 28

| additive | function | Example (mg/tablet) 40 | 41 |
|---|---|---|---|
| polyethylene oxide WSR 303 | gel forming polymer | 18 | 12 |
| pioglitazone hydrochloride (pioglitazone free form) | active ingredient | 1.1 (1) | 1.1 (1) |
| microcrystalline cellulose | gel forming promoter | 0.28 | 0.28 |
| D-mannitol-1 | gel forming promoter | 87.42 | 89.82 |
| D-mannitol-2 | gel forming promoter | 12 | 12 |
| hydroxypropylcellulose | binder | — | 3.6 |
| sodium stearyl fumarate | lubricant | 1.2 | 1.2 |
| Total | | 120 | 120 |

Examples 42-57

In a mortar and according to the formulations of Tables 29-1, 29-2, pioglitazone hydrochloride (fine pulverized product, average particle size about 5 μm), microcrystalline cellulose, D-mannitol and polyethylene oxide (Polyox various viscosity grades, Dow chemical company) were uniformly mixed, sodium stearyl fumarate was added, and the mixture was uniformly mixed to give granules for tableting. The granules were measured by weight 120 mg and tableted by Autograph (AG-1, Shimadzu Corporation) with a 7 mmφ punch to give 20 core tablets containing 1 mg of pioglitazone per tablet.

TABLE 29-1

| additive | function | 42 | 43 | 44 | 45 | 46 | 47 | 48 | 49 | 50 | 51 | 52 | 53 |
|---|---|---|---|---|---|---|---|---|---|---|---|---|---|
| polyethylene oxide WSR N-10 | gel forming polymer | — | 72 | — | — | — | — | — | — | — | — | — | — |
| polyethylene oxide WSR N-80 | gel forming polymer | 72 | — | 72 | — | — | — | — | — | — | — | — | — |
| polyethylene oxide WSR N-750 | gel forming polymer | — | — | — | 42 | 36 | 60 | 24 | 60 | 96 | 60 | 48 | 96 |
| polyethylene oxide WSR N12-K | gel forming polymer | — | — | — | — | — | 12 | 18 | 18 | 18 | 24 | 48 | — |
| polyethylene oxide WSR N60-K | gel forming polymer | — | — | — | 12 | 30 | — | — | — | — | — | — | — |
| polyethylene oxide WSR 301 | gel forming polymer | — | — | — | — | — | — | — | — | — | — | — | 12 |
| polyethylene oxide WSR Coagulant | gel forming polymer | — | — | — | — | — | — | — | — | — | — | — | — |
| polyethylene oxide WSR 303 | gel forming polymer | 18 | 24 | 24 | — | — | — | — | — | — | — | — | — |
| pioglitazone hydrochloride (pioglitazone free form) | active ingredient | 1.1 (1) | 1.1 (1) | 1.1 (1) | 1.1 (1) | 1.1 (1) | 1.1 (1) | 1.1 (1) | 1.1 (1) | 1.1 (1) | 1.1 (1) | 1.1 (1) | 1.1 (1) |
| microcrystalline cellulose | gel forming promoter | 0.28 | 0.28 | 0.28 | 0.28 | 0.28 | 0.28 | 0.28 | 0.28 | 0.28 | 0.28 | 0.28 | 0.28 |
| D-mannitol | gel forming promoter | 27.42 | 21.42 | 21.42 | 63.42 | 51.42 | 45.42 | 75.42 | 39.42 | 3.42 | 33.42 | 21.42 | 9.42 |
| sodium stearyl fumarate | lubricant | 1.2 | 1.2 | 1.2 | 1.2 | 1.2 | 1.2 | 1.2 | 1.2 | 1.2 | 1.2 | 1.2 | 1.2 |
| Total | | 120 | 120 | 120 | 120 | 120 | 120 | 120 | 120 | 120 | 120 | 120 | 120 |

TABLE 29-2

| additive | function | Example (mg/tablet) | | | |
|---|---|---|---|---|---|
| | | 54 | 55 | 56 | 57 |
| polyethylene oxide WSR N-80 | gel forming polymer | — | 12 | — | — |
| polyethylene oxide WSR N-750 | gel forming polymer | — | — | — | 36 |
| polyethylene oxide WSR 205 | gel forming polymer | 84 | — | 60 | — |
| polyethylene oxide WSR N60-K | gel forming polymer | — | — | — | 18 |
| polyethylene oxide WSR 301 | gel forming polymer | 12 | 18 | — | — |
| polyethylene oxide WSR 303 | gel forming polymer | — | — | 12 | — |
| pioglitazone hydrochloride (pioglitazone free form) | active ingredient | 1.1 (1) | 1.1 (1) | 1.1 (1) | 1.1 (1) |
| microcrystalline cellulose | gel forming promoter | 0.28 | 0.28 | 0.28 | 0.28 |
| D-mannitol | gel forming promoter | 21.42 | 87.42 | 45.42 | 63.42 |
| sodium stearyl fumarate | lubricant | 1.2 | 1.2 | 1.2 | 1.2 |
| Total | | 120 | 120 | 120 | 120 |

Comparative Examples 2-14

In a mortar and according to the formulations of Tables 30-1, 30-2, pioglitazone hydrochloride (fine pulverized product, average particle size about 5 μm), microcrystalline cellulose, D-mannitol and polyethylene oxide (Polyox various viscosity grades, Dow chemical company) were uniformly mixed, sodium stearyl fumarate was added, and the mixture was uniformly mixed to give granules for tableting. The granules were measured by weight 120 mg and tabletted by Autograph (AG-1, Shimadzu Corporation) with a 7 mmϕ punch to give 20 core tablets containing 1 mg of pioglitazone per tablet.

Comparative Examples 15-16

In a fluid bed dryer granulator (MP-01, POWREX), and according to the formulation of Table 31, pioglitazone hydrochloride (fine pulverized product, average particle size about 5 μm), microcrystalline cellulose, D-mannitol (in Table 31, D-mannitol-1) and polyethylene oxide (Polyox various viscosity grades, Dow chemical company) were uniformly mixed, and the mixture was granulated while spraying a solution of D-mannitol (in Table 31, D-mannitol-2) and dried in the granulator. The obtained granules were sieved using a 16M sieve to give a sieved powder. To the sieved powder was added sodium stearyl fumarate, and the mixture was admixed by hand in a 10 L plastic bag to give granules for tableting. The granules were measured by weight 120 mg and tabletted by Autograph (AG-1, Shimadzu Corporation) with a 7 mmϕ punch to give 20 core tablets containing 1 mg of pioglitazone per tablet.

TABLE 30-1

| additive | function | Comparative Example (mg/tablet) | | | | | | | |
|---|---|---|---|---|---|---|---|---|---|
| | | 2 | 3 | 4 | 5 | 6 | 7 | 8 | 9 |
| polyethylene oxide WSR N-10 | gel forming polymer | 84 | 96 | — | — | — | — | — | — |
| polyethylene oxide WSR N-80 | gel forming polymer | — | — | 72 | 84 | — | — | — | — |
| polyethylene oxide WSR N-750 | gel forming polymer | — | — | — | — | 60 | 72 | — | — |
| polyethylene oxide WSR 205 | gel forming polymer | — | — | — | — | — | — | 108 | — |
| polyethylene oxide WSR 1105 | gel forming polymer | — | — | — | — | — | — | — | 96 |
| pioglitazone hydrochloride (pioglitazone free form) | active ingredient | 1.1 (1) | 1.1 (1) | 1.1 (1) | 1.1 (1) | 1.1 (1) | 1.1 (1) | 1.1 (1) | 1.1 (1) |
| microcrystalline cellulose | gel forming promoter | 0.28 | 0.28 | 0.28 | 0.28 | 0.28 | 0.28 | 0.28 | 0.28 |
| D-mannitol | gel forming promoter | 33.42 | 21.42 | 45.42 | 33.42 | 57.42 | 45.42 | 9.42 | 21.42 |
| sodium stearyl fumarate | lubricant | 1.2 | 1.2 | 1.2 | 1.2 | 1.2 | 1.2 | 1.2 | 1.2 |
| Total | | 120 | 120 | 120 | 120 | 120 | 120 | 120 | 120 |

TABLE 30-2

| additive | function | Comparative Example (mg/tablet) | | | | |
|---|---|---|---|---|---|---|
| | | 10 | 11 | 12 | 13 | 14 |
| polyethylene oxide WSR 301 | gel forming polymer | 6 | 12 | — | — | — |
| polyethylene oxide WSR Coagulant | gel forming polymer | — | — | 6 | 12 | 36 |

TABLE 30-2-continued

|  |  | Comparative Example (mg/tablet) | | | | |
|---|---|---|---|---|---|---|
| additive | function | 10 | 11 | 12 | 13 | 14 |
| pioglitazone hydrochloride (pioglitazone free form) | active ingredient | 1.1 (1) | 1.1 (1) | 1.1 (1) | 1.1 (1) | 1.1 (1) |
| microcrystalline cellulose | gel forming promoter | 0.28 | 0.28 | 0.28 | 0.28 | 0.28 |
| D-mannitol | gel forming promoter | 111.42 | 105.42 | 111.42 | 105.42 | 81.42 |
| sodium stearyl fumarate | lubricant | 1.2 | 1.2 | 1.2 | 1.2 | 1.2 |
| Total |  | 120 | 120 | 120 | 120 | 120 |

TABLE 31

|  |  | Comparative Example (mg/tablet) | |
|---|---|---|---|
| additive | function | 15 | 16 |
| polyethylene oxide WSR 303 | gel forming polymer | 6 | 12 |
| pioglitazone hydrochloride (pioglitazone free form) | active ingredient | 1.1 (1) | 1.1 (1) |
| microcrystalline cellulose | gel forming promoter | 0.28 | 0.28 |
| D-mannitol-1 | gel forming promoter | 99.42 | 93.42 |
| D-mannitol-2 | gel forming promoter | 12 | 12 |
| sodium stearyl fumarate | lubricant | 1.2 | 1.2 |
| Total |  | 120 | 120 |

Comparative Examples 17-30

In a mortar and according to the formulations of Tables 32-1, 32-2, pioglitazone hydrochloride (fine pulverized product average particle size about 5 μm), microcrystalline cellulose, D-mannitol and polyethylene oxide (Polyox various viscosity grades, Dow chemical company) were uniformly mixed, sodium stearyl fumarate was added, and the mixture was uniformly mixed to give granules for tableting. The granules were measured by weight 120 mg and tableted by Autograph (AG-1, Shimadzu Corporation), with a 7 mmϕ punch to give 20 core tablets containing 1 mg of pioglitazone per tablet.

TABLE 32-1

|  |  | Comparative Example (mg/tablet) | | | | | | | |
|---|---|---|---|---|---|---|---|---|---|
| additive | function | 17 | 18 | 19 | 20 | 21 | 22 | 23 | 24 |
| polyethylene oxide WSR N-10 | gel forming polymer | 84 | — | 84 | — | — | — | — | — |
| polyethylene oxide WSR N-80 | gel forming polymer | — | 72 | — | 72 | — | — | — | 72 |
| polyethylene oxide WSR N-750 | gel forming polymer | — | — | — | — | 24 | 36 | 24 | — |
| polyethylene oxide WSR 205 | gel forming polymer | — | — | — | — | — | — | — | — |
| polyethylene oxide WSR N12-K | gel forming polymer | — | — | — | — | — | — | 6 | — |
| polyethylene oxide WSR N60-K | gel forming polymer | — | — | — | — | — | — | — | — |
| polyethylene oxide WSR 301 | gel forming polymer | — | — | — | — | — | 6 | — | — |
| polyethylene oxide WSR Coagulant | gel forming polymer | — | — | — | — | 6 | — | — | 36 |
| polyethylene oxide WSR 303 | gel forming polymer | 6 | 6 | 12 | 12 | — | — | — | — |
| pioglitazone-hydrochloride (pioglitazone free form) | active ingredient | 1.1 (1) | 1.1 (1) | 1.1 (1) | 1.1 (1) | 1.1 (1) | 1.1 (1) | 1.1 (1) | 1.1 (1) |
| microcrystalline cellulose | gel forming promoter | 0.28 | 0.28 | 0.28 | 0.28 | 0.28 | 0.28 | 0.28 | 0.28 |
| D-mannitol | gel forming promoter | 27.42 | 39.42 | 21.42 | 33.42 | 87.42 | 75.42 | 87.42 | 9.42 |
| sodium stearyl fumarate | lubricant | 1.2 | 1.2 | 1.2 | 1.2 | 1.2 | 1.2 | 1.2 | 1.2 |
| Total |  | 120 | 120 | 120 | 120 | 120 | 120 | 120 | 120 |

TABLE 32-2

| additive | function | Comparative Example (mg/tablet) | | | | | |
|---|---|---|---|---|---|---|---|
| | | 25 | 26 | 27 | 28 | 29 | 30 |
| polyethylene oxide WSR N-80 | gel forming polymer | — | — | 60 | — | — | — |
| polyethylene oxide WSR 205 | gel forming polymer | 60 | 36 | — | 36 | 36 | 36 |
| polyethylene oxide WSR N60-K | gel forming polymer | — | — | — | — | 48 | 42 |
| polyethylene oxide WSR 301 | gel forming polymer | — | — | 12 | 30 | — | — |
| polyethylene oxide WSR Coagulant | gel forming polymer | — | 30 | — | — | — | — |
| polyethylene oxide WSR 303 | gel forming polymer | 24 | — | — | — | — | — |
| pioglitazone hydrochloride (pioglitazone free form) | active ingredient | 1.1 (1) | 1.1 (1) | 1.1 (1) | 1.1 (1) | 1.1 (1) | 1.1 (1) |
| microcrystalline cellulose | gel forming promoter | 0.28 | 0.28 | 0.28 | 0.28 | 0.28 | 0.28 |
| D-mannitol | gel forming promoter | 33.42 | 51.42 | 45.42 | 51.42 | 33.42 | 39.42 |
| sodium stearyl fumarate | lubricant | 1.2 | 1.2 | 1.2 | 1.2 | 1.2 | 1.2 |
| Total | | 120 | 120 | 120 | 120 | 120 | 120 |

Experimental Example 11

The dissolution property of the tablets obtained in Examples 18-57 was measured. One tablet was placed in 900 mL of pH 2.0 KCl/HCl buffer, and evaluation was performed by the USP Paddle Method at 50 rpm, 37° C. After placing the tablet, the dissolution medium was sampled over time, filtered with a non-aqueous filter (0.45 μm), quantified by high-performance liquid column chromatography (HPLC) method under the same conditions as those in Experimental Example 11 except that "YMC-PACK ODS-A, S-5, 12 nm, inner diameter: 4.6 mm, length: 75 mm (manufactured by YMC CO., LTD.)" was used as the column instead of "CAPCELLPAK C18 AQ, 5 μm, inner diameter: 4.6 mm, length: 50 mm (manufactured by Shiseido Co., Ltd.)", and the dissolution rate was calculated. The results are shown in Tables 35-1 to 35-5.

Figure 7:
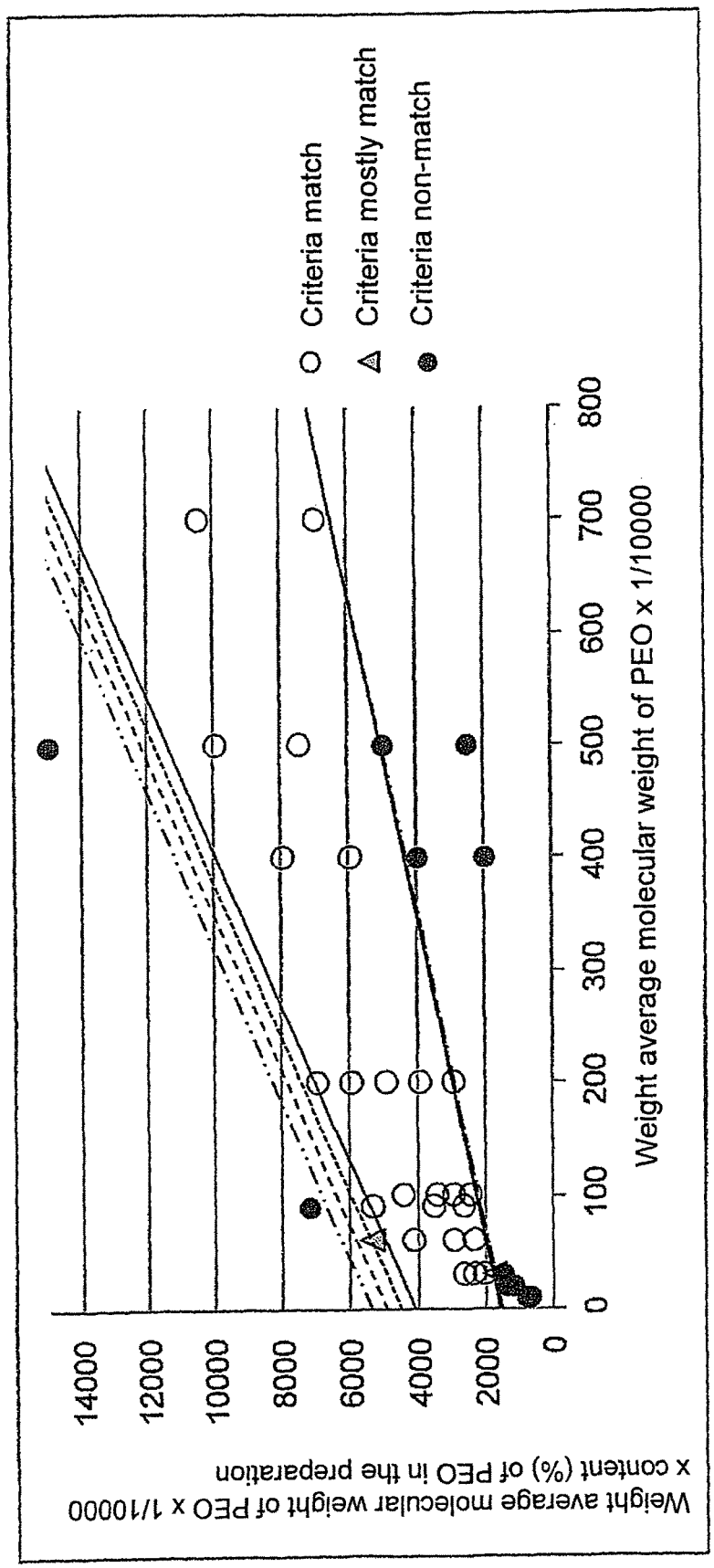
FIG. 7 shows the results in Experimental Examples 11 and 12.
Figure 8:
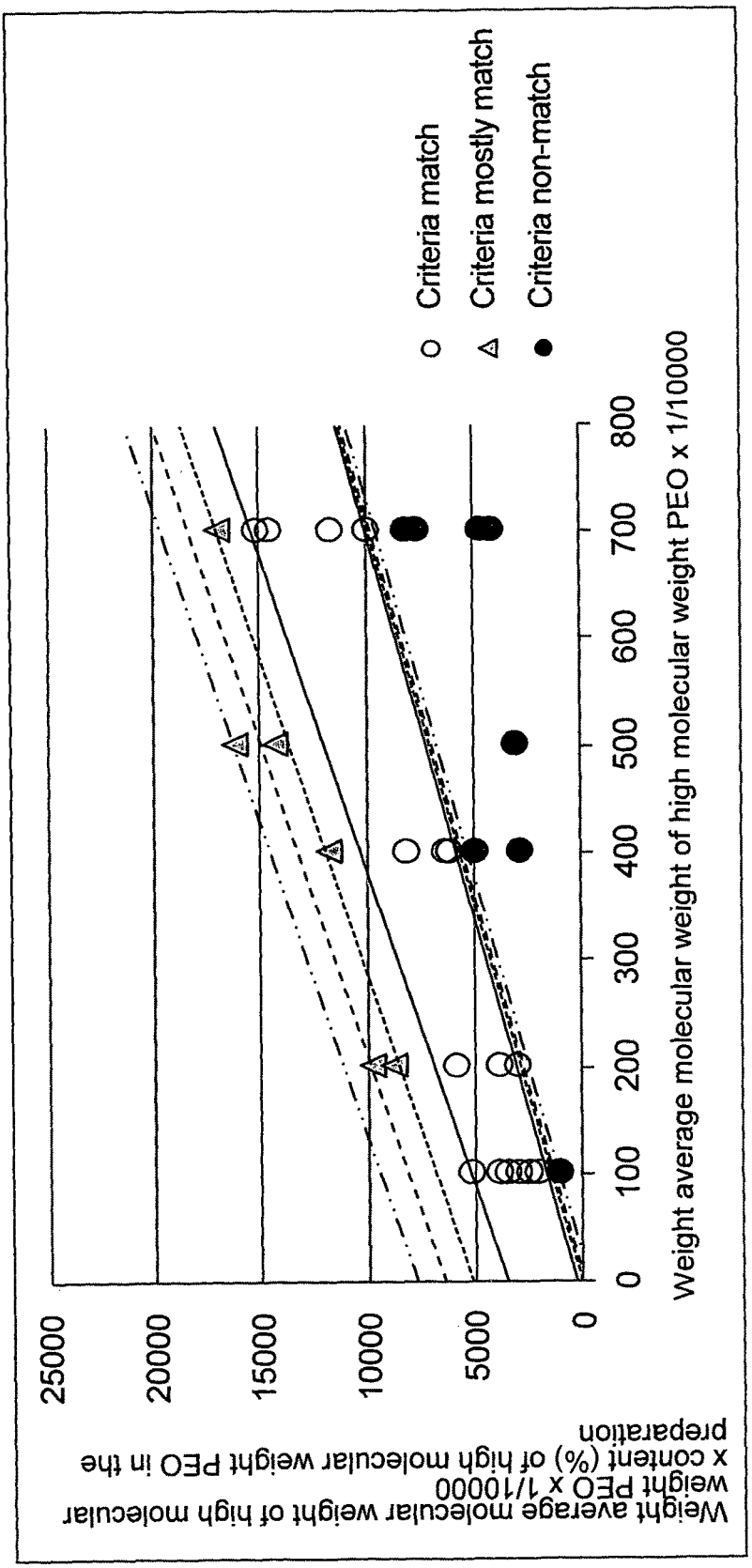
FIG. 8 shows the results in Experimental Examples 11 and 12.

Based on the above-mentioned results, the relationship between "the weight average molecular weight of polyethylene oxide (PEO) ×1/10000" and "its content (%) in the preparation", and the criteria of the dissolution ratio of pioglitazone of "average 25-58% at 2-hour time point, average 60-100% at 4-hour time point, and average 80-110% at 6-hour time point" was analyzed and the results are shown in FIGS. 7, 8.

In Fig, 7, each plot shows the relationship between "weight average molecular weight of PEO ×1/10000" and "weight average molecular weight of PEO ×1/10000× content (%) of PEO in the preparation" in Examples and Comparative Examples using one kind of PEO, wherein white circle means meeting the above-mentioned criteria, triangle means generally meeting the above-mentioned criteria, and black circle means failing to meet the above-mentioned criteria.

The above-mentioned results reveal that a preferable range of the relationship between "weight average molecular weight of PEO ×1/10000" and "content (%) of PEO in the preparation", which is capable of meeting the criteria, can be shown by the following calculation formula.

TABLE 33

| range | preferable | more preferable | still more preferable | further more preferable |
|---|---|---|---|---|
| upper limit | y = 14.5x + 5410 | y = 14.5x + 4970 | y = 14.5x + 4530 | y = 14.5x + 4090 |
| lower limit | y = 7x + 1500 | y = 7x + 1545 | y = 7x + 1590 | y = 7x + 1600 | x: weight average molecular weight of PEO x 1/10000
y: weight average molecular weight of PEO x 1/10000 x content (%) of PEO in the preparation In FIG. 8, each plot shows the relationship between "weight average molecular weight of high molecular weight PEO×1/10000" and "weight average molecular weight of high molecular weight PEO×1/10000×content (%) of high molecular weight PEO in the preparation" in Examples and Comparative Examples using two kinds of PEO having different molecular weights, wherein white circle means meeting the above-mentioned criteria, triangle means generally meeting the above-mentioned criteria, and black circle means failing to meet the above-mentioned criteria. The "high molecular weight PEO" refers to PEO used, which has a higher average molecular weight.

The above-mentioned results reveal that a preferable range of the relationship between "weight average molecular weight of high molecular weight PEO×1/10000" and "content (%) of high molecular weight PEO in the preparation", which is capable of meeting the criteria, can be shown by the following calculation formula.

TABLE 34

| range | preferable | more preferable | still more preferable | further more preferable |
|---|---|---|---|---|
| upper limit | y = 17x + 7700 | y = 17x + 6400 | y = 17x + 5100 | y = 17x + 3500 |
| lower limit | y = 14x − 300 | y = 14x − 100 | y = 14x + 90 | y = 14x + 270 | x: weight average molecular weight of high molecular weight PEO x 1/10000
y: weight average molecular weight of high molecular weight PEO x 1/10000 x content (%) of high molecular weight PEO in the preparation Experimental Example 12

The dissolution property of the tablets obtained in Comparative Examples 2-30 was measured. One tablet was placed in 900 mL of 0.3 M potassium chloride buffer (pH 2.0), and evaluation was performed by the USP Paddle Method at 50 rpm, 37° C. After placing the tablet, the dissolution medium was sampled over time, filtered with a non-aqueous filter (0.45 μm), quantified by high-performance liquid column chromatography (HPLC) method under the conditions similar to those in Experimental Example 111 except that "YMC-PACK ODS-A, S-5, 12 nm, inner diameter: 4.6 mm, length: 75 mm (manufactured by YMC CO., LTD.)" was used as the column instead of "CAPCELLPAK C18 AQ, 5 μm, inner diameter: 4.6 mm, length: 50 mm (manufactured by Shiseido Co., Ltd.)", and the dissolution rate was calculated. The results are shown in Tables 36-1 to 36-5.

TABLE 35-1

| Time (min) | Example 18 | 19 | 20 | 21 | 22 | 23 | 24 | 25 | 26 | 27 | 28 | 29 | object range |
|---|---|---|---|---|---|---|---|---|---|---|---|---|---|
| 120 | 57 | 43 | 33 | 51 | 48 | 35 | 56 | 47 | 34 | 54 | 42 | 38 | 25-58% |
| 240 | 93 | 90 | 72 | 94 | 86 | 73 | 96 | 87 | 69 | 97 | 86 | 77 | 60-100% |
| 360 | 99 | 101 | 100 | 100 | 99 | 98 | 99 | 100 | 94 | 100 | 101 | 99 | 80-110% |

TABLE 35-2

| Time (min) | Example 30 | 31 | 32 | 33 | 34 | 35 | 36 | 37 | 38 | 39 | object range |
|---|---|---|---|---|---|---|---|---|---|---|---|
| 120 | 34 | 54 | 41 | 34 | 30 | 31 | 43 | 37 | 49 | 35 | 25-58% |
| 240 | 67 | 96 | 84 | 71 | 63 | 60 | 72 | 60 | 82 | 63 | 60-100% |
| 360 | 93 | 101 | 99 | 96 | 89 | 87 | 92 | 81 | 100 | 88 | 80-110% |

TABLE 35-3

| Time (min) | Example 40 | 41 | object range |
|---|---|---|---|
| 120 | 43 | 51 | 25-58% |
| 240 | 63 | 76 | 60-100% |
| 360 | 84 | 90 | 80-110% |

TABLE 35-4

| Time (min) | Example 42 | 43 | 44 | 45 | 46 | 47 | 48 | 49 | 50 | 51 | 52 | 53 | object range |
|---|---|---|---|---|---|---|---|---|---|---|---|---|---|
| 120 | 51 | 45 | 34 | 56 | 33 | 44 | 53 | 51 | 32 | 37 | 29 | 33 | 25-58% |
| 240 | 94 | 81 | 69 | 97 | 68 | 87 | 98 | 91 | 70 | 75 | 62 | 70 | 60-100% |
| 360 | 100 | 99 | 96 | 102 | 96 | 99 | 100 | 101 | 95 | 100 | 89 | 97 | 80-110% |

TABLE 35-5

| Time (min) | Example 54 | 55 | 56 | 57 | object range |
|---|---|---|---|---|---|
| 120 | 35 | 31 | 30 | 43 | 25-58% |
| 240 | 71 | 62 | 61 | 85 | 60-100% |
| 360 | 95 | 88 | 88 | 99 | 80-110% |

TABLE 36-1

| Time (min) | Comparative Example 2 | 3 | 4 | 5 | 6 | 7 | 8 | 9 | object range |
|---|---|---|---|---|---|---|---|---|---|
| 120 | 100 | 101 | 100 | 100 | 70 | 61 | 25 | 25 | 25-58% |
| 240 | 99 | 99 | 99 | 99 | 99 | 99 | 55 | 51 | 60-100% |
| 360 | 97 | 97 | 98 | 95 | 99 | 100 | 84 | 79 | 80-110% |

TABLE 36-2

| Time (min) | Comparative Example 10 | 11 | 12 | 13 | 14 | object range |
|---|---|---|---|---|---|---|
| 120 | 100 | 92 | 99 | 81 | 29 | 25-58% |
| 240 | 100 | 100 | 99 | 99 | 51 | 60-100% |
| 360 | 99 | 100 | 99 | 100 | 71 | 80-110% |

TABLE 36-3

| Time (min) | Comparative Example 15 | 16 | object range |
|---|---|---|---|
| 120 | 100 | 66 | 25-58% |
| 240 | 99 | 89 | 60-100% |
| 360 | 99 | 96 | 80-110% |

TABLE 36-4

| Time (min) | Comparative Example 17 | 18 | 19 | 20 | 21 | 22 | 23 | 24 | object range |
|---|---|---|---|---|---|---|---|---|---|
| 120 | 102 | 99 | 99 | 82 | 90 | 71 | 97 | 28 | 25-58% |
| 240 | 103 | 98 | 100 | 100 | 100 | 100 | 101 | 56 | 60-100% |
| 360 | 102 | 97 | 100 | 98 | 99 | 100 | 100 | 82 | 80-110% |

TABLE 36-5

| Time (min) | Comparative Example 25 | 26 | 27 | 28 | 29 | 30 | object range |
|---|---|---|---|---|---|---|---|
| 120 | 25 | 24 | 95 | 24 | 22 | 25 | 25-58% |
| 240 | 45 | 47 | 101 | 45 | 45 | 48 | 60-100% |
| 360 | 67 | 68 | 101 | 66 | 67 | 70 | 80-110% |

INDUSTRIAL APPLICABILITY

The sustained-release preparation containing pioglitazone or a salt thereof of the present invention has the following characteristics and is useful in the pharmaceutical field. (1) A sustained release of a medicament can be done; even if the dose is low, stable efficacy can be expected, since the medicament is released in a sustained manner. (2) The maximum drug concentration (Cmax) can be controlled (e.g., can be suppressed lower than immediate-release preparation). (3) The area under plasma concentration-time curve (AUC) equivalent to that of immediate-release preparation can be achieved. (4) A preparation capable of standing physical stimulation due to eating (unsusceptible to stimulation by eating) is hoped to be provided.

This application is the U.S. National Stage of PCT/JP2012/077662, filed Oct. 19, 2012, which claims priority from patent application No. 2011-232302 filed on Oct. 21, 2011 in Japan, the contents of which are incorporated in full herein.

The invention claimed is:

1. A sustained-release preparation comprising pioglitazone or a salt thereof, polyethylene oxide and a gel forming promoter,
which has a dissolution rate of pioglitazone averaging 25-58% at the 2-hour time point, and averaging 60-100% at the 4-hour time point, in a dissolution test according to the 50 rpm USP Paddle Method and using pH 2.0 KCl/HCl buffer at 37° C. as a test solution, wherein the polyethylene oxide is
1) contained such that a product of the weight average molecular weight $\times 1/10000$ and the content (%) of polyethylene oxide in the preparation is from $(7 \times M + 1500)$ to $(14.5 \times M + 5410)$, wherein M shows a value calculated by a weight average molecular weight of polyethylene oxide $\times 1/10000$ when one kind of polyethylene oxide is used; or
2) contained such that a product of the weight average molecular weight $\times 1/10000$ and the content (%) of polyethylene oxide having the highest average molecular weight among the polyethylene oxides used in the preparation is from $(14 \times M - 300)$ to $(17 \times M + 7700)$, wherein M shows a value calculated by a weight average molecular weight of polyethylene oxide having the highest average molecular weight $\times 1/10000$ when two or more kinds of polyethylene oxides having different average molecular weights are used, and
wherein the sustained-release preparation contains 0.05-20 wt % pioglitazone or a salt thereof, 10-90 wt % polyethylene oxide and 2.5-80 wt % gel forming promoter, and
wherein the sustained-release preparation delays onset or suppresses progression of Alzheimer's disease.

2. The sustained-release preparation according to claim 1, wherein the gel forming promoter is a water-soluble hydrophilic base or water-insoluble hydrophilic base.

3. The sustained-release preparation according to claim 2, wherein the water-soluble hydrophilic base is one kind or a combination of two or more kinds selected from lactose, glucose, mannitol and trehalose, and the water-insoluble hydrophilic base is one kind or a combination of two or more kinds selected from starch, partially pregelatinized starch, crospovidone, crystalline cellulose, carmellose calcium and carmellose.

4. The sustained-release preparation according to claim 1, which is a tablet.

5. The sustained-release preparation according to claim 4, which has a tablet weight of 60-600 mg.

6. The sustained-release preparation according to claim 1, wherein the pioglitazone or a salt thereof is pioglitazone hydrochloride.

7. The sustained-release preparation according to claim 1, wherein the pioglitazone or a salt thereof has an average particle size of 1 to 25 μm.

8. A method of delaying onset or suppressing progression of Alzheimer's disease, comprising orally administering the sustained-release preparation according to claim 1 to a subject in need of the administration thereof.

9. The sustained-release preparation according to claim 1, comprising 0.1-8 mg of pioglitazone; or a salt of pioglitazone corresponding to 0.1-8 mg as pioglitazone.

10. The sustained-release preparation according to claim 1, comprising 0.1 mg, 0.3 mg, 0.5 mg, 0.8 mg, 2.8 mg or 5.2 mg of pioglitazone; or a salt of pioglitazone corresponding to 0.1 mg, 0.3 mg, 0.5 mg, 0.8 mg, 2.8 mg or 5.2 mg as pioglitazone.

* * * * *